(12) United States Patent
Ufkes et al.

(10) Patent No.: US 12,029,825 B2
(45) Date of Patent: Jul. 9, 2024

(54) FIXED POSITION HYBRID GERMICIDAL IRRADIATION APPARATUS, METHOD, AND SYSTEM

(71) Applicant: UD Innovations, LLC, Sullivan's Island, SC (US)

(72) Inventors: Philip J. Ufkes, Sullivan's Island, SC (US); Jeffery L. Deal, Charleston, SC (US)

(73) Assignee: UD Innovations, LLC, Sullivan's Island, SC (US)

(*) Notice: Subject to any disclaimer, the term of this patent is extended or adjusted under 35 U.S.C. 154(b) by 882 days.

(21) Appl. No.: 17/031,613

(22) Filed: Sep. 24, 2020

(65) Prior Publication Data

US 2021/0113724 A1    Apr. 22, 2021

Related U.S. Application Data

(63) Continuation-in-part of application No. 16/787,339, filed on Feb. 11, 2020, now Pat. No. 11,364,313, which is a continuation-in-part of application No. 15/869,417, filed on Jan. 12, 2018, now Pat. No. 10,556,025.

(Continued)

(51) Int. Cl.
*A61L 2/10* (2006.01)
*A61L 2/24* (2006.01)

(52) U.S. Cl.
CPC .............. *A61L 2/10* (2013.01); *A61L 2/24* (2013.01); *A61L 2202/11* (2013.01); *A61L 2202/14* (2013.01); *A61L 2202/25* (2013.01)

(58) Field of Classification Search
CPC .......... A61L 2/10; A61L 2/24; A61L 2202/14; A61L 2202/11; A61L 9/20;

(Continued)

(56) References Cited

U.S. PATENT DOCUMENTS 9,744,255 B2 * 8/2017 Stibich ...................... A61L 2/10
2002/0015662 A1   2/2002 Hlavinka
(Continued)

FOREIGN PATENT DOCUMENTS

| WO | 2007095543 A2 | 8/2007 |
| WO | 2015116876 A1 | 8/2015 |
| WO | 2016044759 A1 | 3/2016 |

OTHER PUBLICATIONS

Extended European Search Report, European application No. 18738922.6. dated Sep. 8, 2020. European Patent Office, Munich, DE.
(Continued)

*Primary Examiner* — Sean E Conley
*Assistant Examiner* — Brendan A Hensel
(74) *Attorney, Agent, or Firm* — Gregory Finch; Finch Paolino, LLC

(57) ABSTRACT

A hybrid germicidal irradiation apparatus, method, and system for multi-band germicidal irradiation. A first plurality of emitters and a second plurality of emitters may be coupled to a housing configured to be coupled to a ceiling of an interior room. The first plurality of emitters and the second plurality of emitters may be operable to emit UV-C radiation at a wavelength of about 265 nanometers and near-UV radiation at a wavelength of about 405 nanometers, respectively. One or more radiation sensors are configured to measure the amount of UV-C light or near UV-C light reflected from a target surface. A controller may be communicably engaged with the radiation sensors to calculate an amount of UV-C radiation and near-UV radiation delivered to a target surface or interior space.

20 Claims, 18 Drawing Sheets

Related U.S. Application Data

(60) Provisional application No. 62/445,415, filed on Jan. 12, 2017.

(58) Field of Classification Search
CPC ........... A61L 2209/111; A61L 2202/25; H05B 47/155; H05B 47/125; H05B 45/20; Y02B 20/40
See application file for complete search history.

(56) References Cited

U.S. PATENT DOCUMENTS

| | | | |
|---|---|---|---|
| 2011/0168898 A1 | 7/2011 | Statham et al. | |
| 2011/0272595 A1* | 11/2011 | Neister | A61L 9/22 250/435 |
| 2013/0330235 A1 | 12/2013 | Stibich et al. | |
| 2015/0217012 A1 | 8/2015 | Garner et al. | |
| 2016/0375163 A1 | 12/2016 | Hawkins et al. | |
| 2017/0173195 A1* | 6/2017 | Stibich | A61L 2/24 |
| 2019/0247528 A1* | 8/2019 | Rodriguez | A61L 2/26 |

OTHER PUBLICATIONS

First Examination Report, European application No. 18738922.6. dated Jul. 13, 2021. European Patent Office, Munich, DE.
Summons to attend oral proceedings pursuant to Rule 115(1) EPC. European patent application No. 18738922.6. Date of mailing Nov. 21, 2022. European Patent Office, Munich, DE.

\* cited by examiner

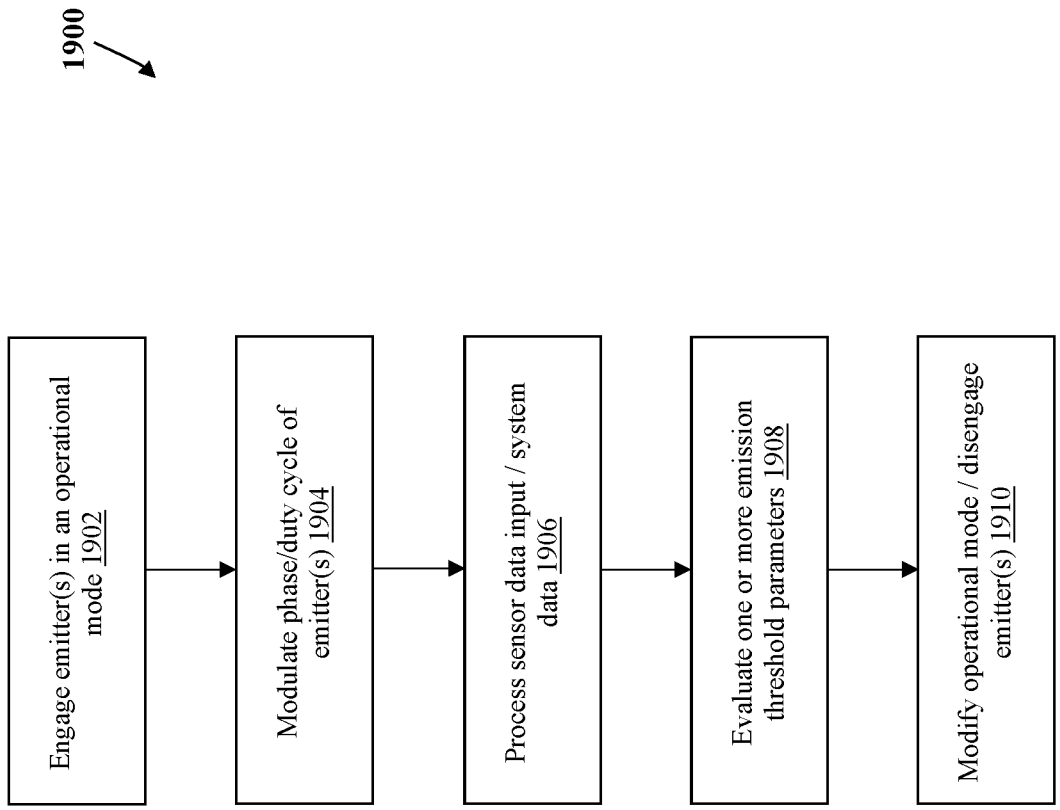

FIXED POSITION HYBRID GERMICIDAL IRRADIATION APPARATUS, METHOD, AND SYSTEM

CROSS-REFERENCE TO RELATED APPLICATIONS

This application is a continuation-in-part of U.S. patent application Ser. No. 16/787,339, filed on Feb. 11, 2020 entitled "FIXED POSITION HYBRID GERMICIDAL IRRADIATION APPARATUS, METHOD, AND SYSTEM", which is a continuation-in-part of U.S. patent application Ser. No. 15/869,417, filed on Jan. 12, 2018 entitled "FIXED POSITION HYBRID GERMICIDAL IRRADIATION APPARATUS, METHOD, AND SYSTEM", which claims the benefit of U.S. Provisional Application Ser. No. 62/445,415, filed on Jan. 12, 2017 entitled "FIXED POSITION HYBRID GERMICIDAL IRRADIATION APPARATUS, METHOD AND SYSTEM," the disclosures of which are hereby incorporated in their entireties at least by virtue of this reference.

FIELD

This invention relates to methods and devices for bacterial, fungal and/or viral sterilization and disinfection, and is more particularly directed to an apparatus, method and system for ultraviolet and near-ultraviolet germicidal irradiation.

BACKGROUND

Ultraviolet germicidal irradiation (UVGI) is a disinfection method that uses short-wavelength ultraviolet (UV-C) light to kill or inactivate microorganisms. One mechanism by which UV-C deactivates microorganisms is by destroying nucleic acids and disrupting their DNA, leaving them unable to perform vital cellular functions. The administration of UV-C radiation is becoming widely adopted by many hospitals as a more effective and reliable means of surface disinfection, as compared to the use of chemical cleaning agents alone. The effectiveness of germicidal UV-C irradiation depends on factors such as the length of time a microorganism is exposed to UV-C, the intensity and wavelength of the UV-C radiation, the presence of particles that can protect the microorganisms from UV, and a microorganism's ability to withstand UV-C during its exposure. In air and surface disinfection applications, the UV effectiveness is estimated by calculating the UV dose to be delivered to the microbial population. A method of calculating UV dose is as follows: UV dose $\mu Ws/cm^2$=UV intensity $\mu W/cm^2 \times$Exposure time (seconds).

Germicidal UV for disinfection is most typically generated by a mercury-vapor lamp. Low-pressure mercury vapor has a strong emission line at 254 nm, which is within the range of wavelengths that demonstrate strong disinfection effect. The optimal wavelengths for disinfection are close to 265 nm. UV-C LEDs use semiconductors to emit light between 255 nm-280 nm. The wavelength emission is tunable by adjusting the material of the semiconductor. The use of LEDs that emit a wavelength more precisely tuned to the maximal germicidal wavelength results in greater microbe deactivation per amp of power, maximization of microbial deactivation for the available, less ozone production, and less materials degradation.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

An aspect of the present disclosure is a mounted, typically ceiling mounted, hybrid germicidal irradiation disinfection apparatus comprising a substantially rectangular housing having dimensions of approximately two feet in width and four feet in length; a first plurality of emitters coupled to the substantially rectangular housing, the first plurality of emitters operable to emit UV-C radiation at a wavelength of about 265 nanometers; a second plurality of emitters coupled to the substantially rectangular housing, the second plurality of emitters operable to emit near-UV radiation at a wavelength of about 405 nanometers; at least one visible light emitter coupled to the substantially rectangular housing; at least one germicidal radiation sensor coupled to the substantially planar array surface; a controller being housed in the substantially rectangular housing, the controller being operably engaged with the first plurality of emitters, the second plurality of emitters, the at least one visible light emitter, and the at least one germicidal radiation sensor.

Another aspect of the present disclosure is a method for room disinfection using germicidal radiation comprising: installing, in an interior ceiling grid, a hybrid germicidal irradiation disinfection apparatus (disinfection fixture), the disinfection fixture having a first plurality of emitters operable to emit UV-C radiation at a wavelength of about 265 nanometers and a second plurality of emitters operable to emit near-UV radiation at a wavelength of about 405 nanometers, a ranging sensor, and a controller; measuring, with the ranging sensor, the distance to the closest object (surface) in the room; calculating, with the controller, an air gap compensation variable in response to ranging sensor measurement; delivering, with the first plurality of emitters and the second plurality of emitters, dual band radiation to a target zone of the room; receiving, with at least one germicidal radiation sensor, an amount of radiant energy reflected from the first zone of the room; measuring, with the processor, a kill dose threshold based on germicidal radiation sensor input and air gap compensation.

Yet another aspect of the present disclosure is a system for room disinfection using germicidal radiation comprising one or more disinfection fixtures and an optional remotely mounted germicidal radiation sensor (remote sensor) operating in a communications network, the one or more disinfection fixtures comprising: a substantially rectangular housing having dimensions of approximately two feet in width and four feet in length; a first plurality of emitters coupled to the substantially rectangular housing, the first plurality of emitters operable to emit UV-C radiation at a wavelength of about 265 nanometers; a second plurality of emitters coupled to the substantially rectangular housing, the second plurality of emitters operable to emit radiation at a near-UV wavelength of about 405 nanometers; at least one visible light emitter coupled to the substantially rectangular housing; at least one, optional, germicidal radiation sensor coupled to the substantially planar array surface (alternatively, the system may employ a networked remote sensor directed to one or more target areas); a controller being housed in the substantially rectangular housing, the controller being operably engaged with the first plurality of emitters, the second plurality of emitters, the at least one visible light emitter, and the at least one germicidal radiation sensor;

and, a remote interface, the remote interface being communicably engaged with the controller of the at least one portable UV-C disinfection apparatus, the optional remote sensor; and, a database, the database being communicably engaged with the controller and the remote interface.

Certain aspects of the present disclosure provide for a germicidal disinfection apparatus comprising a housing; at least one first emitter coupled to the housing and configured to emit ultraviolet light at a first wavelength in the range of 207 to 225 nanometers; at least one second emitter coupled to the housing and configured to emit ultraviolet light at a second wavelength between 200 and 280 nanometers; and a controller operably engaged with the at least one first emitter to pulse a first emission of ultraviolet light comprising the first wavelength and operably engaged with the at least one second emitter to pulse a second emission of ultraviolet light comprising the second wavelength, wherein the controller is configured to selectively modulate a duty cycle and phase of the at least one first emitter and the at least one second emitter.

In accordance with certain embodiments, the germicidal disinfection apparatus may further comprise at least one third emitter coupled to the housing and configured to emit visible light at a third wavelength of greater than 400 nanometers. The germicidal disinfection apparatus may further comprise at least one sensor configured to detect the presence of an occupant within an emission zone of the at least one first emitter and at least one second emitter, the at least one sensor being operably engaged with the controller to communicate a sensor input. In accordance with certain embodiments, the controller may be configured to selectively modulate the at least one first emitter and the at least one second emitter to pulse the first emission of ultraviolet light and the second emission of ultraviolet light in phase or out of phase. In certain embodiments, the first wavelength may be 222 nm and the second wavelength may be 265 nm. The controller may be configured to modulate the duty cycle of the at least one first emitter according to at least one control setting in response to the sensor input from the at least one sensor. In accordance with certain embodiments, the controller may be configured to modulate the duty cycle of the at least one second emitter according to at least one control setting in response to the sensor input from the at least one sensor.

Further aspects of the present disclosure provide for a method for controlling microorganisms in an interior environment comprising installing, to a ceiling of an interior room, a germicidal disinfection apparatus; pulsing, in a first mode of operation, a first emission of ultraviolet light from the at least one first emitter and the at least one second emitter; and pulsing, in a second mode of operation, a second emission of ultraviolet light from the at least one first emitter and the at least one second emitter; wherein the first mode of operation comprises modulating the duty cycle and phase of the at least one first emitter and the at least one second emitter according to a first plurality of control settings, and wherein the second mode of operation comprises modulating the duty cycle and phase of the at least one first emitter and the at least one second emitter according to a second plurality of control settings.

In accordance with certain aspects of the present disclosure, the method for controlling microorganisms in an interior environment may further comprise calculating a radiation dose delivered by the at least one first emitter and the at least one second emitter. The method may further comprise terminating an emission from the at least one first emitter or the at least one second emitter in response to the radiation dose being greater than or equal to at least one maximum radiation exposure limit for an occupant. The method may further comprise modulating the duty cycle and/or phase of one or both of the at least one first emitter and the at least one second emitter according to a kinetic model associated with at least one microorganism. The method may further comprise modulating the pulse width of an emission from the at least one first emitter and/or an emission from the at least one second emitter according to the kinetic model associated with the at least one microorganism.

Further aspects of the present disclosure provide for a germicidal disinfection system comprising a housing; at least one first emitter coupled to the housing and configured to emit ultraviolet light at a first wavelength in the range of 207 to 225 nanometers; at least one second emitter coupled to the housing and configured to emit ultraviolet light at a second wavelength between 200 and 280 nanometers; and a controller operably engaged with the at least one first emitter and the at least one second emitter, the controller comprising at least one microprocessor configured to perform one or more operations for controlling an emission of ultraviolet light from the at least one first emitter and the at least one second emitter, wherein the one or more operations comprise operations for selectively modulating a duty cycle and phase of the at least one first emitter and the at least one second emitter.

In accordance with certain embodiments, the one or more operations of the controller may further comprise operations for modulating the duty cycle of the at least one first emitter and the at least one second emitter in response to a sensor input from at least one occupant sensor communicably engaged with the controller. The one or more operations of the controller may further comprise operations for modulating the duty cycle of the at least one first emitter and the at least one second emitter in response to a sensor input from at least one radiation sensor communicably engaged with the controller. The one or more operations of the controller may further comprise operations for modulating the duty cycle and/or phase of one or both of the at least one first emitter and the at least one second emitter according to a kinetic model associated with at least one microorganism.

Still further aspects of the present disclosure provide for a germicidal disinfection system comprising at least one first emitter configured to emit ultraviolet light at a first wavelength in the range of 207 to 225 nanometers; at least one second emitter configured to emit ultraviolet light at a second wavelength between 200 and 280 nanometers; and a controller operably engaged with the at least one first emitter and the at least one second emitter to pulse an emission of ultraviolet light comprising the first wavelength from the at least one first emitter and pulse an emission of ultraviolet light comprising the second wavelength from the at least one second emitter according to one or more control parameters, wherein the one or more control parameters comprise parameters for modulating a duty cycle of the at least one first emitter and the at least one second emitter and parameters for modulating a phase of the at least one first emitter and the at least one second emitter.

In accordance with certain embodiments, the germicidal disinfection system may further comprise at least one third emitter configured to emit visible light at a third wavelength of greater than 400 nanometers. In accordance with certain embodiments, the one or more operations of the controller may further comprise operations for modulating the duty cycle of one or both of the at least one first emitter and the at least one second emitter in response to a sensor input from at least one sensor communicably engaged with the controller. In certain embodiments, the at least one sensor is selected from the group consisting of a radiation sensor, a ranging sensor, a motion sensor, an imaging sensor, a camera, and an acoustic transducer.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE DRAWINGS

The above and other objects, features and advantages of the present disclosure will be more apparent from the following detailed description taken in conjunction with the accompanying drawings, in which:

FIG. 19 is a process flow diagram of a method for controlling microorganisms in an interior environment, in accordance with an embodiment.

DETAILED DESCRIPTION

Figure 1:
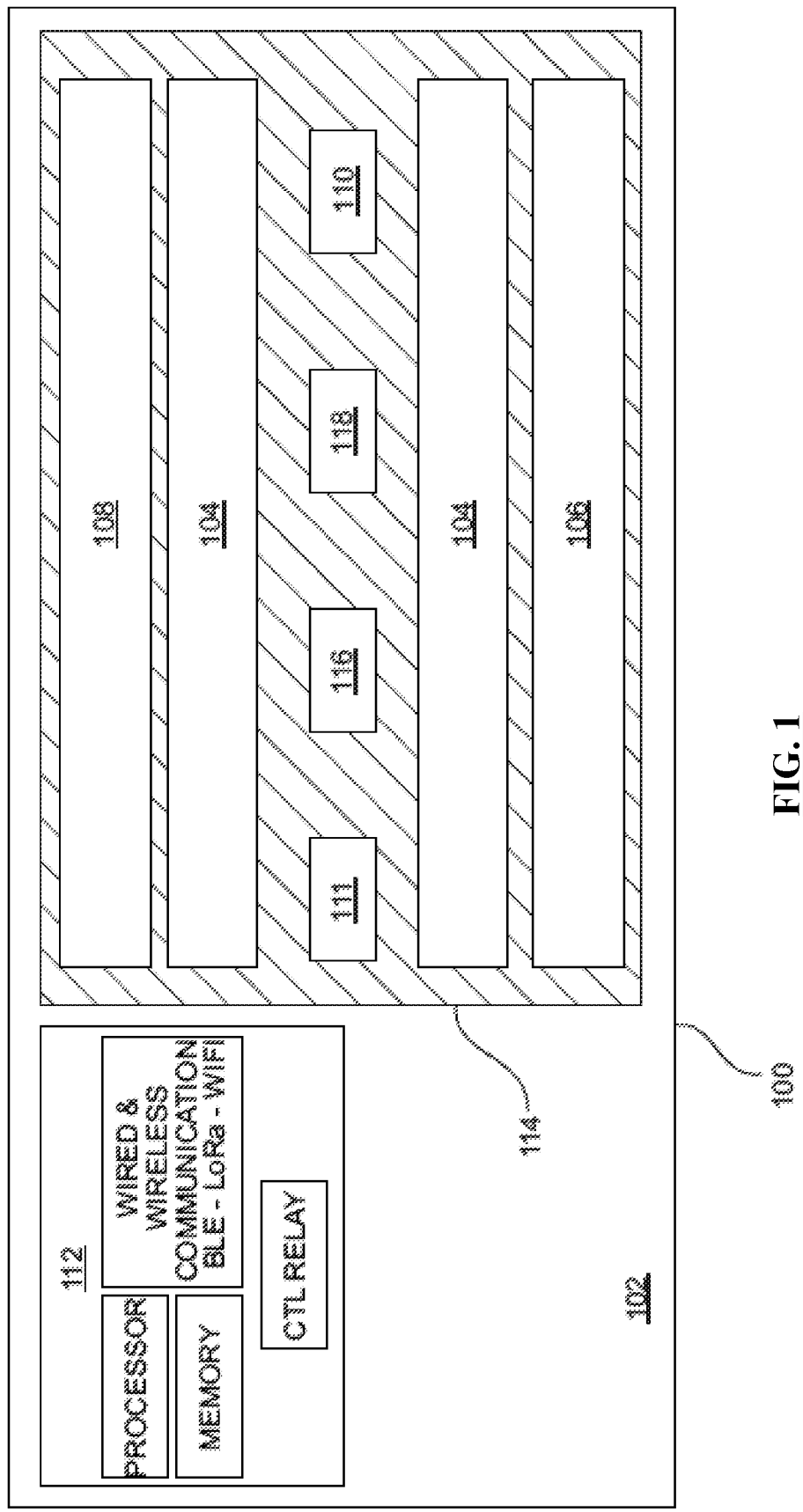
FIG. 1 is a system diagram of a hybrid germicidal irradiation disinfection apparatus in an embodiment of the present disclosure.

Exemplary embodiments are described herein to provide a detailed description of the present disclosure. Variations of these embodiments will be apparent to those of skill in the art. It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein. Moreover, certain terminology is used in the following description for convenience only and is not limiting. For example, the words "right," "left," "top," "bottom," "upper," "lower," "inner" and "outer" designate directions in the drawings to which reference is made. The word "a" is defined to mean "at least one." The terminology includes the words above specifically mentioned, derivatives thereof, and words of similar import.

Following below are more detailed descriptions of various concepts related to, and embodiments of, inventive methods, devices and systems configured to provide for a UV light fixture configured to enable contactless germicidal disinfection of microorganisms in the air and on surfaces.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes. The present disclosure should in no way be limited to the exemplary implementation and techniques illustrated in the drawings and described below.

Where a range of values is provided, it is understood that each intervening value, to the tenth of the unit of the lower limit unless the context clearly dictates otherwise, between the upper and lower limit of that range and any other stated or intervening value in that stated range is encompassed by the invention. The upper and lower limits of these smaller ranges may independently be included in the smaller ranges, and are also encompassed by the invention, subject to any specifically excluded limit in a stated range. Where a stated range includes one or both of the endpoint limits, ranges excluding either or both of those included endpoints are also included in the scope of the invention.

As used herein, "exemplary" means serving as an example or illustration and does not necessarily denote ideal or best.

As used herein, the term "includes" means includes but is not limited to, the term "including" means including but not limited to. The term "based on" means based at least in part on.

Embodiments of the present disclosure further provide for a more cost-effective solution to retrofit overhead light fixtures with UV-C and near-UV emitters in hospital-wide deployments. Embodiments of the present disclosure provide for a disinfection fixture that reduces exposure time by varying the intensity and wavelength of the UV-C administered. Like UVGI, near-UV (violet-blue) light, particularly 405 nm light, has significant antimicrobial properties against a wide range of bacterial and fungal pathogens. Unlike UVGI, near-UV is safe for continuous use in occupied environments. Embodiments of the present disclosure provide for a hybrid arrangement of UVGI and near-UV emitters for the optimum deployment of both UVGI and near-UV in a closed-loop disinfection process and general area illumination.

Referring now to FIG. 1, a diagrammatic representation of a hybrid germicidal irradiation disinfection apparatus (disinfection fixture) 100 is shown. According to an embodiment, disinfection fixture 100 is generally comprised of a fixture housing 102, a visible light emitter 104, a 265 nanometers (nm) UV-C emitter 106, a 405 nanometers (nm) near-UV emitter 108, a 265 nm germicidal radiation sensor (UV-C Sensor) 110, a 405 nm germicidal radiation sensor (Near-UV Sensor) 111, a controller 112, a UV transmittable lens 114, a ranging sensor 116, and an occupant sensor 118. According to an embodiment, fixture housing 102 contains the emitter and circuitry components, wiring, and installation fittings of disinfection fixture 100. Fixture housing 102 may be two feet by two feet or two feet by four feet in dimension. Fixture housing 102 should be configured such that it may be installed in a standard-sized commercial ceiling grid and should be installing using standard commercial wiring. The standard sizing and wiring of fixture housing 102 enable disinfection fixture 100 to be easily retrofitted into hospitals and other commercial structures. Fixture housing 102 may be constructed of rigid or flexible material, such as plastic, metal, metal alloy, and the like. Alternatively, variations in the fixture housing 102 materials, emitters and construction dimensions may be altered as needed for a specific application (e.g. wall-mounting, free-hanging installation, outside of a ceiling grid). Fixture housing 102 is configured to house an electrical relay to at least one visible light emitter 104 and one or more 265 nm UV-C emitter 106 and/or one or more 405 nm near-UV emitter 108. Visible light emitter 104 should be of a spectrum and color temperature typically used for commercial interior lighting, for example 2650-kelvin. The disinfection fixture 100 provides dual functionality as both a commercial light source and a germicidal radiation emitter. UV-C emitters 106 and 405 nm emitters 108 are preferably UV-C LEDs and near-UV LEDs, respectively. In an alternative embodiment, UV-C emitters 106 and near UV emitters 108 are electronic gas-discharge lamps, including but not limited to low-pressure mercury-vapor lamps, high-pressure mercury vapor lamps, xenon lamps, mercury-xenon lamps, pulsed-xenon lamps, and deuterium lamps. In another embodiment, UV-C emitters 106 and near UV emitters 108 may be CFL lamps and halogen lamps.

UV-C 265 nm emitters 106 and 405 nm emitters 108 may be distributed in a linear arrangement and direct UV-C and near-UV radiation in a targeted or distributed beam, enabling higher intensity emission with less power consumption as compared to an omnidirectional bulb. The higher intensity generated by focusing a beam of germicidal radiation using a linear array, rather than an omnidirectional transmission generated by a mercury-vapor bulb or circular LED array, has the dual benefits of reducing exposure time in the dosage calculation and conserving energy. UV-C and near-UV emitters may be calibrated to various wavelength emissions within a known range of wavelengths that demonstrate strong disinfection effect.

As discussed above, emitters 106 and emitters 108 emit radiation at wavelengths of 265 nm and 405 nm respectively. Each wavelength displays its own kinetics of a kill curve for target microorganisms. It is anticipated that emitters 104 and emitters 106 may pulse emission in-phase (i.e. emit light at the same time), or out of phase (i.e. emit light at opposite times), or operate independently, which may modify the kinetics of each wavelength's respective kill curve such that a dual wavelength emission will reduce the overall time required to achieve a kill dose as compared to a single wavelength emission. Likewise, various modulation schema may be employed between emitters 104 and emitters 106 in order to optimize the kinetics of the kill curve for a given microorganism (e.g. viruses, bacteria, and spores); thereby reducing the amount of time required to achieve a kill dose for the target microorganism.

According to an embodiment, UV-C sensor 110, Near-UV sensor 111, ranging sensor 116 and occupant sensor 118 are coupled to a face portion of the fixture housing 102. Optionally, ranging sensor 116 and occupant sensor 118 may be combined into a single sensor or sensor suite. UV-C sensor 110 is a closed loop sensor operable to measure the amount of UV-C energy reflected from the target surface back to the UV-C sensor 110. Near-UV sensor 111 is also a closed loop sensor operable to measure the amount of near-UV energy reflected from the target surface back to the Near-UV sensor 111. UV-C sensor 110 and Near-UV sensor 111 may be a single sensor or an array of multiple sensors. UV-C sensor 110 and Near-UV sensor 111 may be a single dual-band sensor operable to measure radiation wavelengths of about 265 nm and about 405 nm. UV-C sensor 110 and Near-UV sensor 111 are operably engaged with controller 112 to communicate the amount of UV-C and near-UV radiation (single or dual band) collected by the sensor(s).

Controller 112 has a set of instructions stored thereon to measure a "kill dose" according to the amount of reflected UV-C and/or near UV radiation collected by UV-C sensor 114 and kill dose parameters stored in memory. Controller 112 may calibrate various kill dose thresholds depending on the specific disinfection application. For example, viruses may require a lower kill dose, while bacteria may require a higher kill dose, and spores may require yet a higher kill dose.

Controller 112 may operate in communication with ranging sensor 116 to more accurately measure a kill dose delivered from emitters 106 and/or emitters 108. The UV-C energy collected by UV-C sensor 110 might not accurately represent the amount of UV-C energy reflected by the target surface due to the distance, or air gap, between the target surface and UV-C sensor 110. This is due to the fact that germicidal radiation loses intensity as a function of distance travelled; therefore, the measured reflected energy at UV-C sensor 110 is less than the actual reflected energy received by the target surface as a function of the distance between the target surface and UV-C sensor 110. Ranging sensor 116 may be operably engaged with controller 112 to calculate an "air gap compensation" to virtually relocate UV-C sensor 110 to the nearest surface. This can be accomplished mathematically by correcting for the reduction in UV-C energy as a function of distance. Ranging sensor 116 may be comprised of, for example, one or more sensors capable of detecting the presence and location of objects within the sensor range without physical contact, such as sonic ranging, scanning ranging, and/or visible or infrared-based light sensors. Ranging sensor 116 is operably engaged to detect the distance to the nearest object in the zone of each UV-C sensor 110. Controller 112 may adjust the kill dose threshold of reflected energy received by UV-C sensor 110 in accordance with the distance input defined by ranging sensor 116. In the absence of ranging sensor 116, controller 112 may enable a manual input by a user to define the desired air gap adjustment.

As a safety precaution to prevent a user from exposure to UV-C radiation, occupant sensor 118 may be operably engaged with controller 112 to disengage emitter 106 when an occupant is detected in a room. As with ranging sensor 116, occupant sensor 118 may be comprised of, for example, one or more sensors capable of detecting the presence and location of objects within the sensor range without physical contact, such as sonic ranging sensors, scanning ranging sensors, and/or visible or infrared-based light sensors. Lens 114 covers the perimeter of fixture housing 102 and protects the emitters 104, 106 and 108 from debris and dust. Lens 114 may be constructed from any UV-C transmittable material and may be configured as a Fresnel lens such that lens 114 may be substantially planar in shape.

Figure 2:
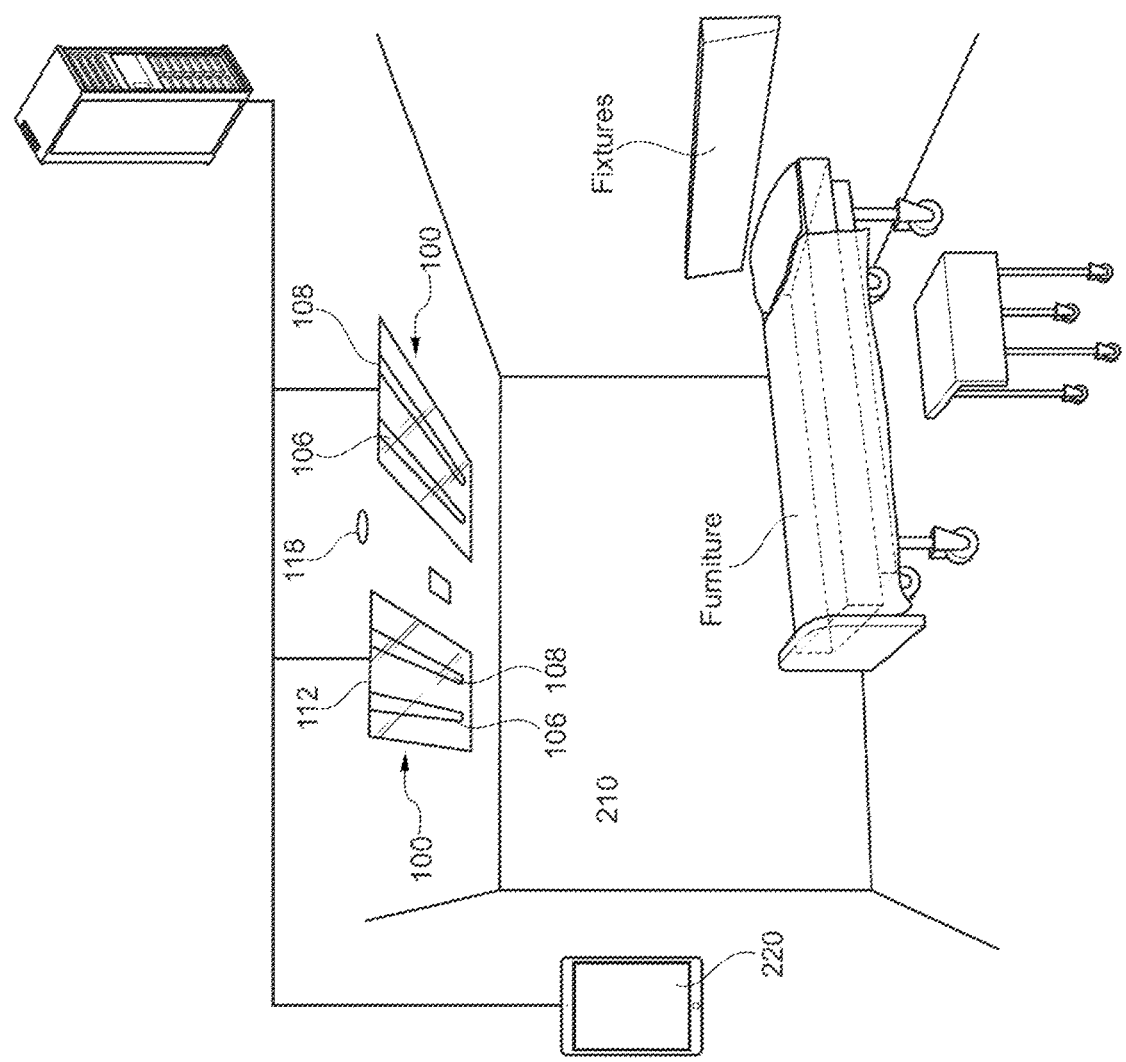
FIG. 2 is a system drawing of communication flow during a room disinfection by an embodiment of a hybrid germicidal irradiation disinfection apparatus.

Referring now to FIG. 2, a system drawing of communication flow during a disinfection cycle started via a remote interface is shown. According to an embodiment, disinfection fixture 100 administers germicidal radiation to a target zone via one or more emitters 106 and emitters 108. In a preferred embodiment, UV-C emitters 106 are calibrated to emit short wave UV-C radiation at a wavelength of 265 nm, and emitters 108 are calibrated to emit short wave near-UV radiation at a wavelength of 405 nm. Remote Interface 220 is networked to controller 112 via a wireline or wireless communication interface, such as Bluetooth or LoRa. Remote interface 220 may be a tablet computer, desktop computer, smart phone, laptop computer, wireless I/O device, and the like. Remote interface 220 associates a room identifier 210 with the disinfection fixture 100. A room identifier 210 may be a scanned barcode or RFID tag. This association ensures that all data collected during the disinfection cycle is attributed to the target room. Controller 112 receives the signal from remote interface 220 to begin the disinfection cycle. Occupant sensor 118 is activated to detect movement in the room. During this safety check, movement detected in the room will inhibit the initial ranging sensor scan. In the embodiment shown in FIG. 2, the occupant sensor 118 is alternatively affixed remotely to one of the ceiling panels in the target room.

Figure 3:
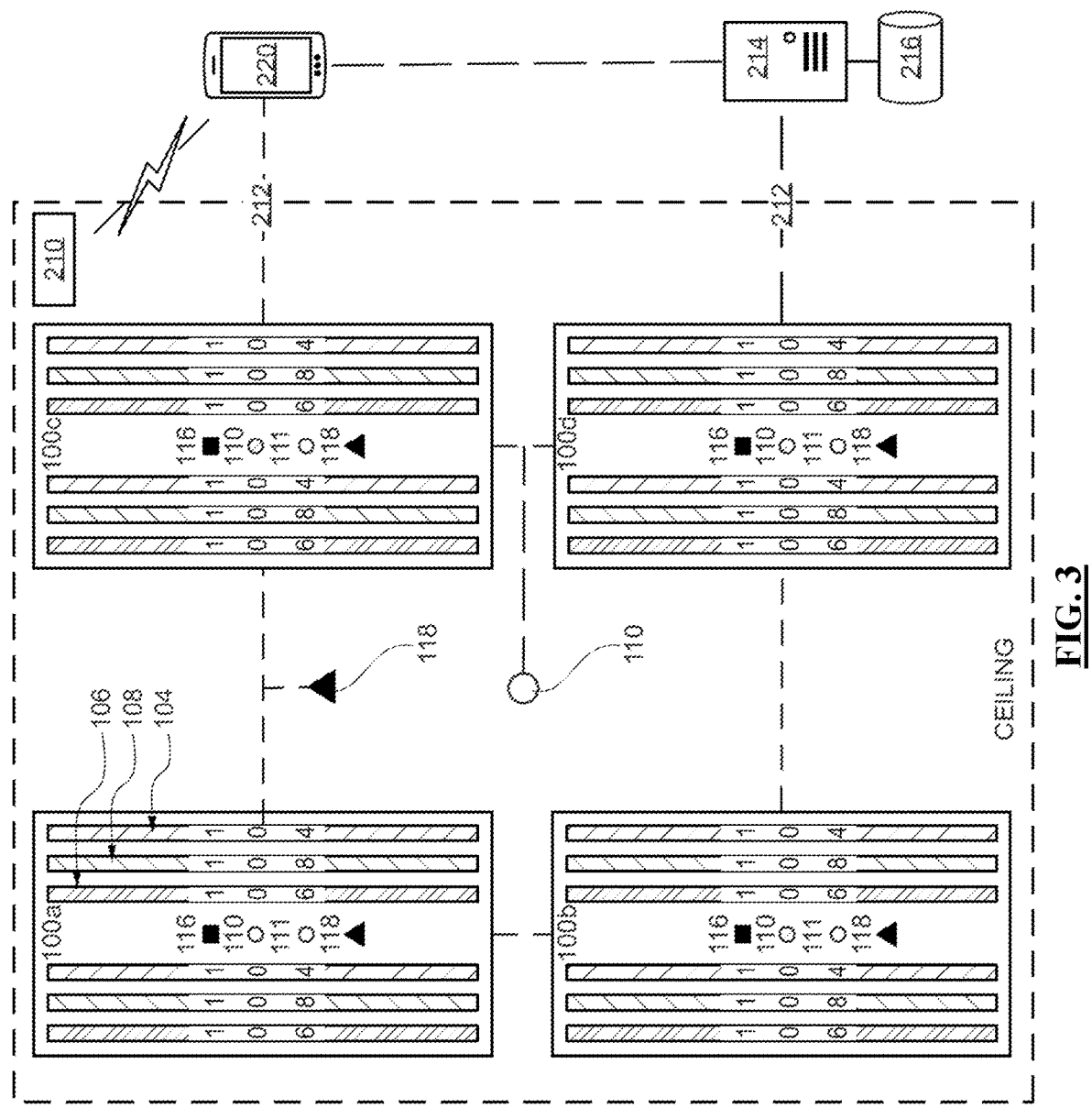
FIG. 3 is a system diagram of the integration of an embodiment of a hybrid germicidal irradiation disinfection apparatus, a remote germicidal radiation sensor, a remote interface and hospital server.

Referring now to FIG. 3, an illustrative system view of a networked implementation of multiple disinfection fixtures is shown. In an embodiment, multiple networked disinfection fixtures 100a-d are communicably linked to one another and one or more hospital systems via a LoRa, WiFi, or Bluetooth communication link. Alternatively, disinfection fixtures 100a-d may be hardwired and communicate through a hospital Ethernet network. Remote interface 220 sends a command to disinfection fixtures 100a-d to begin a room disinfection sequence. Each one of disinfection fixtures 100a-d is dedicated to a specific zone of the room and implements a safety protocol by signaling occupant sensor 118 to monitor each target zone for movement or occupants (i.e. infrared signatures). If no occupants are detected, the integrated disinfection fixtures 100a-d begin the disinfection cycle. The UV-C sensors measure the UV-C energy reflected from the target zone and/or the near-UV sensors measure the near-UV energy reflected from the target zone depending on the selected disinfection sequence. The ranging sensors measure the distance to the nearest object in the zone, and virtually relocate the germicidal radiation sensors to the location of the nearest object surface to compensate for the air gap between the surface of the nearest object and the surface of the germicidal radiation sensors (as discussed in FIGS. 4-6). Controller 112 continuously monitors germicidal sensor data against a predetermined kill dose threshold to determine whether a kill dose has been administered to the target zone. Once a target zone has received an effective kill dose, emitters 106 and/or 108 are disengaged or redirected to a different zone. The disinfection cycle is complete once all zones in the target room have received the designated radiation kill dose. Controller 112 sends a notification to remote interface 220 upon completion of the disinfection cycle. Remote interface 220 correlates disinfection data with room ID 210. The disinfection data as well as other system data is stored in hospital server 214 and is accessible by remote interface 220.

Figure 4:
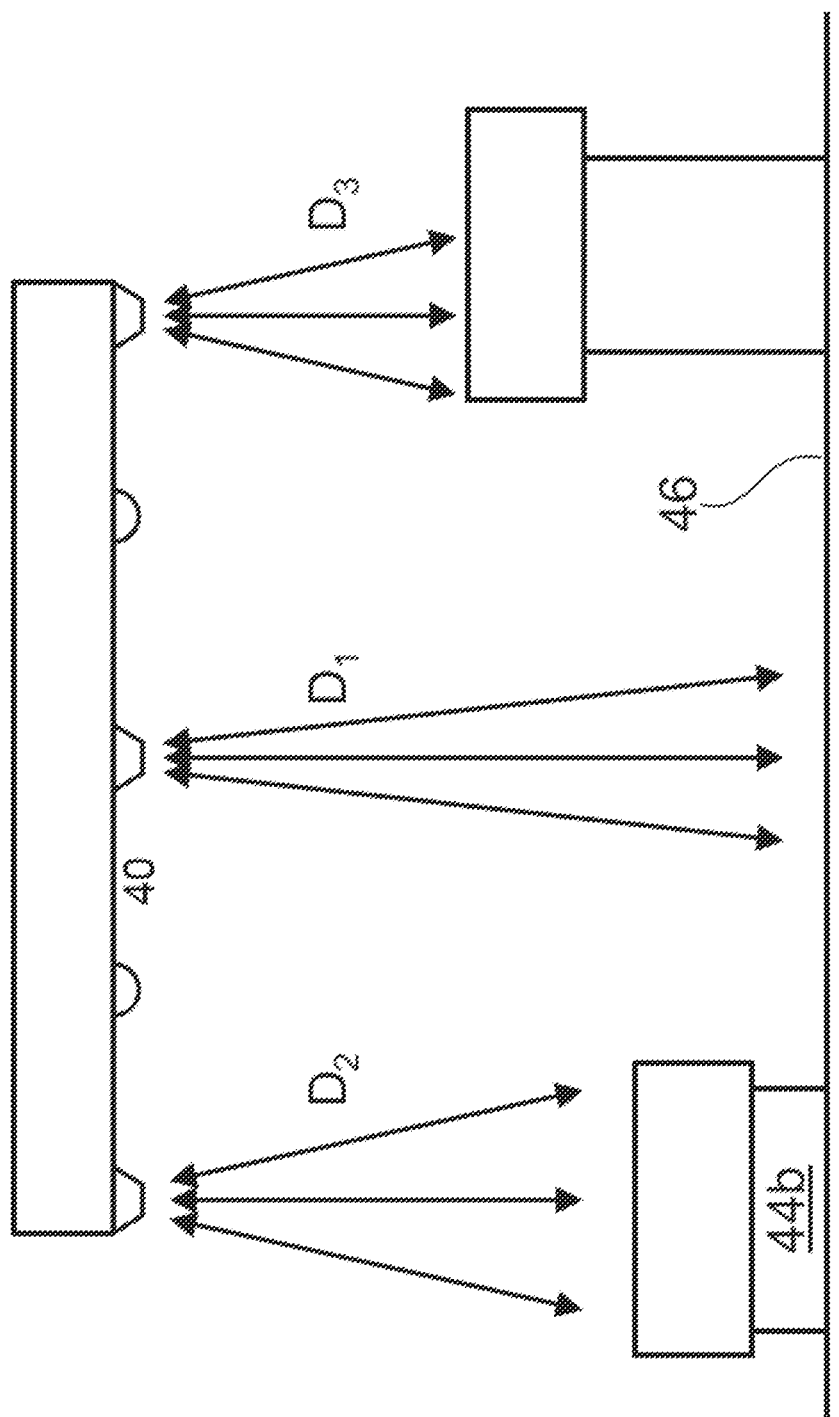
FIG. 4 is a functional diagram of a ranging sensor according to an embodiment.
Figure 5:
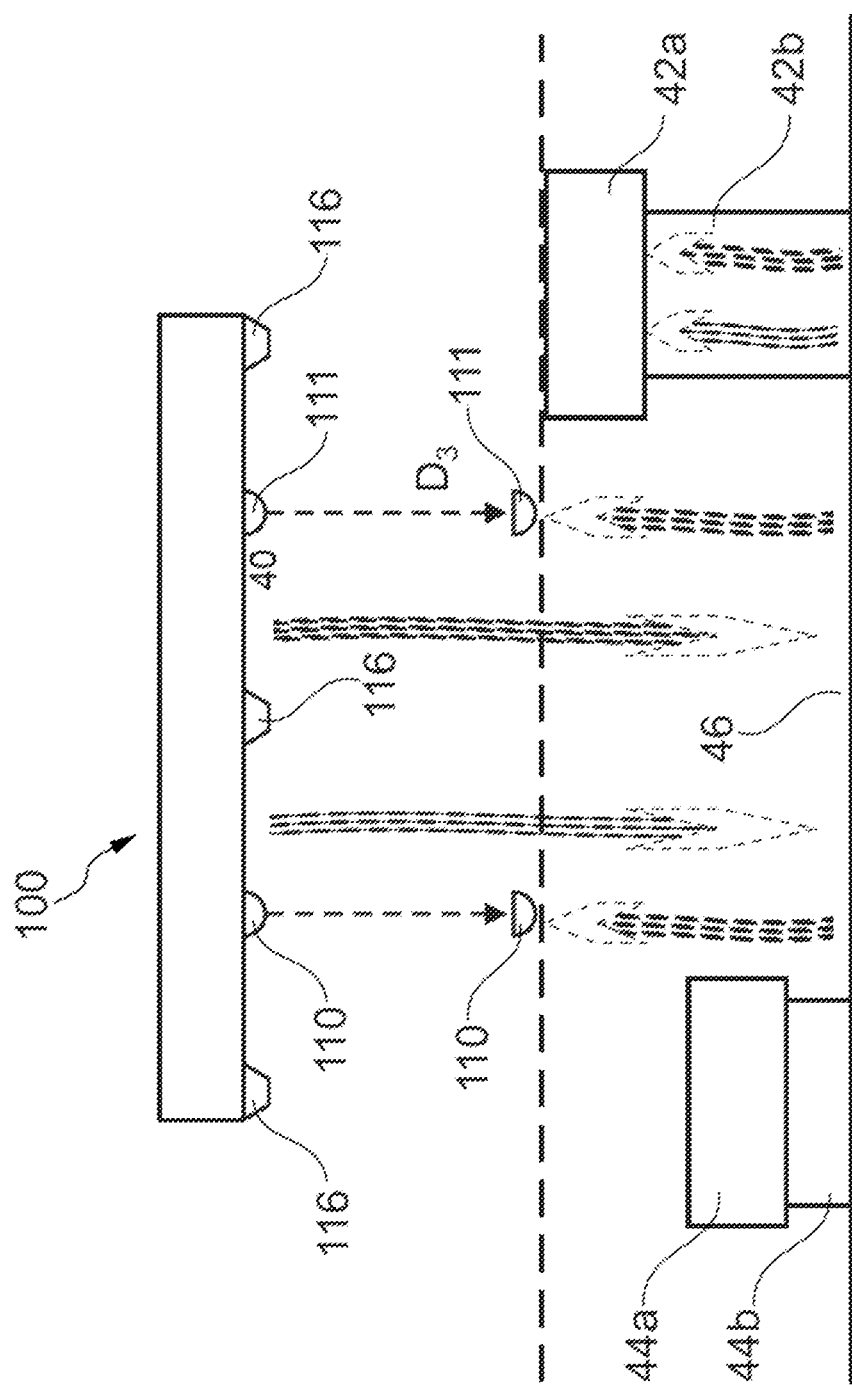
FIG. 5 is a functional diagram of an air gap compensation measurement (virtual germicidal radiation sensor location), according to an embodiment.

Referring now to FIGS. 4 and 5, a functional illustration of an air gap compensation calculation by disinfection fixture 100 is shown. According to an embodiment, ranging sensor(s) 116 measures the distance from disinfection fixture 100 surface 40 to the floor surface 46, $D_1$, and to the leading surface of the closest furniture and fixtures in the room 42a, $D_3$ and 44a, $D_2$. In this illustration, surface 42a at distance $D_3$ is the closest surface to disinfection fixture 100 and is used to define the air gap compensation setting for germicidal radiation sensors 110 and 111. The back side of the object, surface 42b (i.e. the "dark" side of the object relative to disinfection fixture 100) is disinfected by receiving germicidal radiation reflected back from the floor surface 46. As discussed above, a kill dose is measured by the amount of radiation reflected from the target surface to germicidal radiation sensors 110 and/or 111. The kill dose is measured using reflected radiation, rather than direct energy, in order to ensure that the dark side of surfaces in the target room (i.e. surfaces not receiving direct exposure of germicidal radiation) are sufficiently disinfected. The amount of reflected radiation can be accurately measured from the leading edge of the closest object in the room 42a to infer the dosage received by the dark side of object 42b.

Referring now to FIG. 5, the distance $D_3$ represents the air gap between germicidal radiation sensors 110 and 111 and the leading edge of the closest object in the room 42a. The intensity of the reflected radiation is reduced between $D_3$ and $D_1$, as the intensity of radiation diminishes with distance. Therefore, measuring a kill dose at surface 40 results in an over measurement of radiation, which in turn results in overexposure of germicidal radiation and increased time for disinfection fixture 100 to complete a disinfection cycle. Disinfection fixture 100 mitigates over-exposure and minimizes disinfection time by virtually relocating germicidal radiation sensors 110 and/or 111 to surface 42a by executing an air gap compensation algorithm. This enables disinfection fixture 100 to emit the minimum required amount of germicidal irradiation necessary for an effective kill dose per the selected disinfection cycle.

Figure 6:
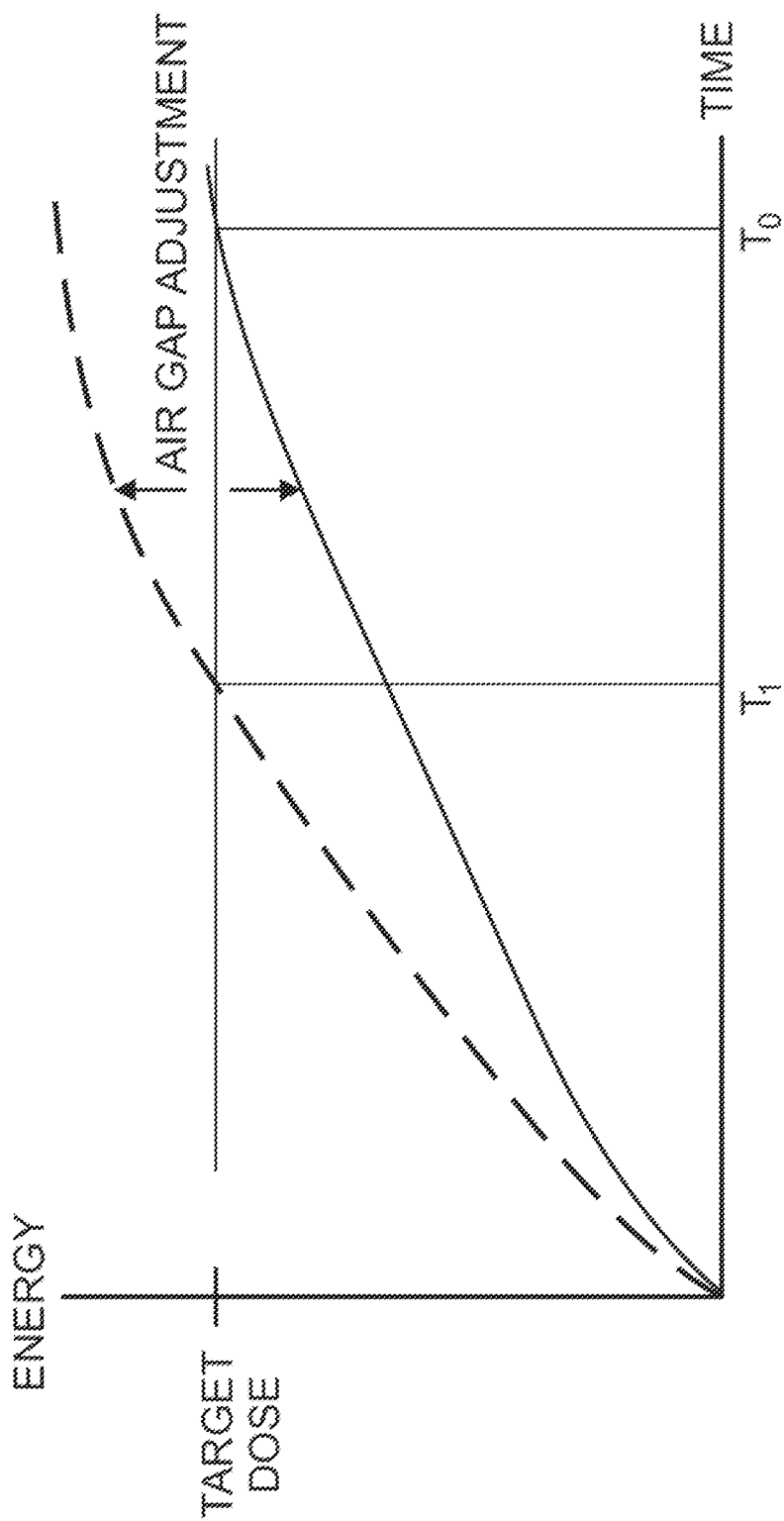
FIG. 6 is a plot of a target dose calculation, as calculated with and without compensation for air gap.

FIG. 6 further illustrates the above concepts of FIG. 5 by plotting the reflected energy received by germicidal radiation sensor 110 (on the y-axis) as a function of time (on the x-axis) in order to reach a target dose of reflected energy. Where UV-C sensors 110 have not been virtually relocated to compensate for air gap, the time required to reach an effective kill dose is shown on the graph as $T_0$. Where UV-C sensors 110 have been virtually relocated to compensate for air gap, the time required to reach an effective kill dose is shown on the graph as $T_1$. The delta between $T_0$ and $T_1$ represents the amount of time saved during the disinfection cycle when compensating for air gap between the germicidal sensor and the location of the nearest object in the zone.

Figure 7:
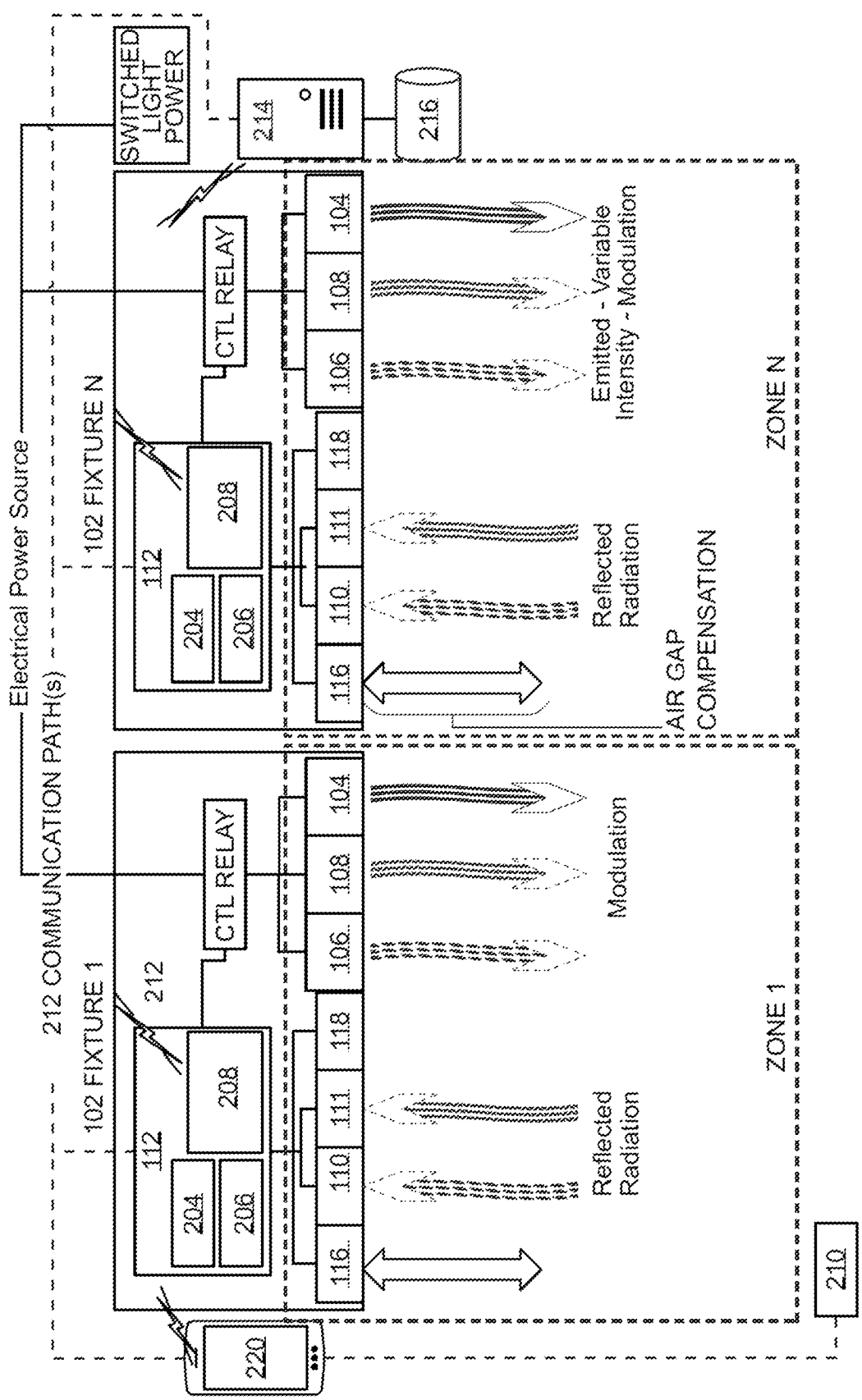
FIG. 7 is a functional diagram of an embodiment of a hybrid germicidal irradiation disinfection apparatus.

Referring now to FIG. 7, a system diagram of a ceiling-mounted disinfection fixture is shown. According to an embodiment, disinfection fixture 100 administers germicidal radiation to a target zone via one or more UV-C emitters 106 and one or more near-UV emitters 108. In a preferred embodiment, as mentioned above, UV-C emitters 106 are calibrated to emit short wave UV-C radiation at a wavelength of 265 nm, and near-UV emitters 108 are calibrated to have a wavelength emission of 405 nm. Remote interface 220 is communicably engaged with controller 112 via a wireless communication interface, such as Bluetooth or WiFi. Remote interface 220 may be a tablet computer, smart phone, laptop computer, wireless I/O device, and the like. Remote interface 220 associates a room identifier 210 with a target room for disinfection. Remote interface 220 may include a user workflow configured to validate that a target room is prepped properly for disinfection and that all the steps in the disinfection workflow have been completed. A room identifier 210 may be a scanned barcode or RFID tag. Remote interface 220 communicates a request to begin a disinfection cycle to controller 112. Processor 204 processes the request to begin a disinfection cycle. Processor 204 executes instructions for ranging sensor 116 to scan a target Zone 1 to determine the closest object in the zone. The data from ranging sensor 116 is stored in memory 206, along with room ID 210. Processor 204 executes instructions to measure air gap compensation to calibrate UV-C sensor 110 according to the data from ranging sensor 116. Processor 204 executes instructions to initiate UV-C emitters 104 and/or near-UV emitters 106 to emit germicidal radiation to target Zone 1 thru N. Radiation reflected from the target Zone 1 through N is reflected back to array housing 102 and is collected by UV-C sensor 110. UV-C sensor 110 sends dosage data to processor 204. Processor 204 executes instructions to measure a kill dose according to UV-C reflectivity data and air gap compensation variables. Once a threshold dosage value has been received by UV-C sensor 110, processor 204 executes instructions to discontinue radiation emission by emitters 106. In parallel the same closed-loop disinfection process may be performed, depending on the selected disinfection cycle, by processor 204 for the desired dose of near-UV germicidal irradiation using ranging sensor 116, near-UV sensor 111 and emitters 108.

Processor 204 executes instructions to store dosage data from each zone in memory 206. The dosage data is time stamped and communicated to hospital server 214 using wireless communication chip set 208 via hospital network 212. Hospital server 214 stores information retrieved from controller 112 in hospital database 216. This information can be utilized by hospital server 214 to determine the health of the hospital, audit cleaning activities, as well as monitor the health and status of a facility wide deployment. Communication chip set 208 may be a LoRa chipset, and hospital network 212 may be configured as a low power wide area network (LPWAN) to reduce burden on the hospital's Wi-Fi network. Processor 204 may communicate a confirmation to remote interface 220 to confirm disinfection of the target room is complete.

Figure 8:
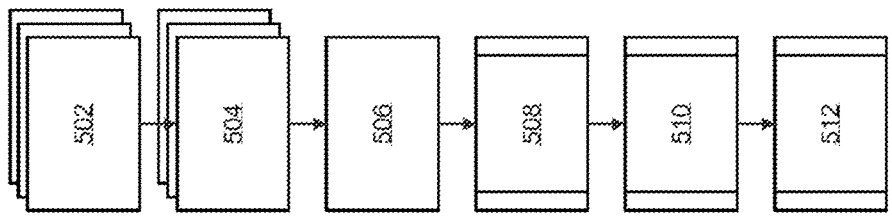
FIG. 8 is a functional block diagram of the setup process of an embodiment of a hybrid germicidal irradiation disinfection apparatus.

Referring now to FIG. 8, a block diagram illustrating how to set up a disinfection fixture is shown. According to an embodiment, the disinfection fixture(s) may be retrofitted into a ceiling grid by uninstalling an existing fluorescent light fixture(s) 502 and installing one or more disinfection fixtures 504. The installed disinfection fixtures may be communicably coupled with the hospital server 506 through Bluetooth or LoRa utilizing a wireless chip in the controller unit or alternatively the disinfection fixtures may be hardwired to a network (e.g. Ethernet). The hospital server associates each disinfection fixture with a specific Room ID 508 and all data regarding room disinfection such as fixture placement and germicidal irradiation dosage calculation is saved under an association with specific room ID 508. This information is saved in the disinfection fixture's memory and may be accessed and saved on the hospital server. Alternatively, the disinfection fixtures memory may be accessed by a remote interface. The disinfection cycle may be engaged by a remote interface such as a tablet computer, laptop, or smartphone by establishing a wireless communication link (such as Bluetooth, WiFi, or LoRa) with the controller of the disinfection fixture 510. The remote interface links disinfection fixtures with the same room ID to an assigned room 512.

Figure 9:
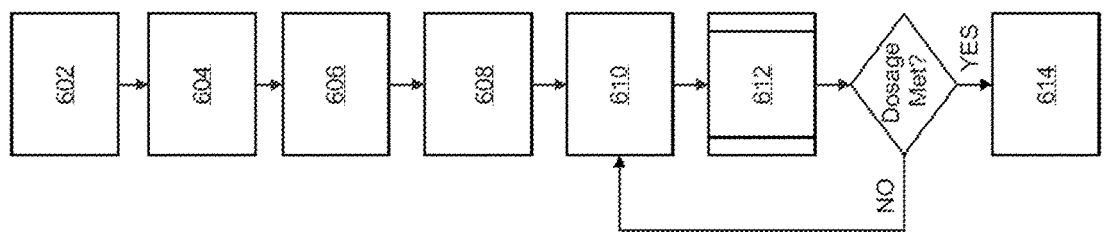
FIG. 9 is a functional block diagram of the disinfection process of an embodiment of a hybrid germicidal irradiation disinfection apparatus.

Referring now to FIG. 9, a block diagram illustrating the steps of the disinfection cycle is shown. A remote interface such as a tablet, smartphone, or laptop sends a request for disinfection 602 to the disinfection fixture(s) via a communications network. An occupant sensor verifies the target room is unoccupied and transmits a success message to a processor associated with a disinfection fixture 604. One or more ranging sensors measures the distance to the closest surface in the zone, and the processor computes an air gap compensation parameter for the germicidal radiation sensor 606. LED emitters emit radiation at wavelengths of 265 nm and/or 405 nm to target area 608. Emitters may pulse emission in-phase (i.e. emit light at the same time), or out of phase (i.e. emit light at opposite times) or deliver single mode germicidal radiation depending on the selected disinfection cycle. Emitted radiation is reflected back from surfaces in the zone to germicidal sensors, which measure the reflected dual band germicidal radiation 610 and transmit the data to the processor. The processor executes instructions to calculate a kill dose for the target zone based on the sensor data and air gap compensation algorithm 612. Once a zone has received a kill dose, the controller disengages the emitters and ends the zone radiation 614 in accordance with the selected disinfection mode.

Embodiments of the present disclosure provide for multiple modes of operation, including normal mode, in which the disinfection fixture as shown and described above may operate as a standard lighting fixture to emit non-UV visible light to illuminate a room, and several disinfection modes depending on the desired level of disinfection, the organism involved, and the occupation of the target space. Two such modes may include: Disinfection and Sustainment. The Disinfection Mode follows the flow outlined above by FIG. 9. Disinfection Mode is selected when the target room is unoccupied and standard cleaning has been performed. Both germicidal emitters 106 and 108 may be energized and the visible light emitters 104 may be depowered.

Sustainment Mode may be selected after the room has been disinfected to maintain a desired level of disinfection or when the room is occupied by a patient with a compromised immune system or active infection such as MRSA. In this mode the visible light emitters will operate via the remote interface 220. The output level (brightness and intensity) of the visible light emitters 104 may be varied by pulse-width modulation or active current control in response to commands from the remote interface 220. The UV-C Emitters 106 will remain off as the room is occupied. The near-UV emitters 108 may remain continuously on thereby providing continuous air and surface disinfection. The output level of the near-UV emitters 108 may be varied by pulse-width modulation or active current control in response to commands from the remote interface 220.

Figure 10:
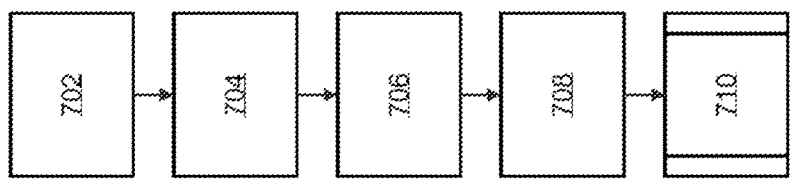
FIG. 10 is a functional block diagram illustrating the storing of data from the disinfection process of an embodiment of a hybrid germicidal irradiation disinfection apparatus.

Referring now to FIG. 10, a block diagram illustrating a method of storing dosage data associated with a room disinfection is shown. According to an embodiment, the processor communicates all dosage data related to a room disinfection to be stored in memory of the controller 702. The room dosage data is time-stamped 704 and associated with a room ID in a database. The time-stamped dosage information may be communicated to a hospital server 706 via a hospital network. The hospital server associates the time-stamped dosage information with the room ID of the disinfection fixtures 708. The time-stamped dosage data may also be accessed by or sent as a notification to a remote interface 710. This information can be utilized by quality control to determine the health of the hospital, as well as monitor the health and status of a facility wide deployment.

Figure 11A:
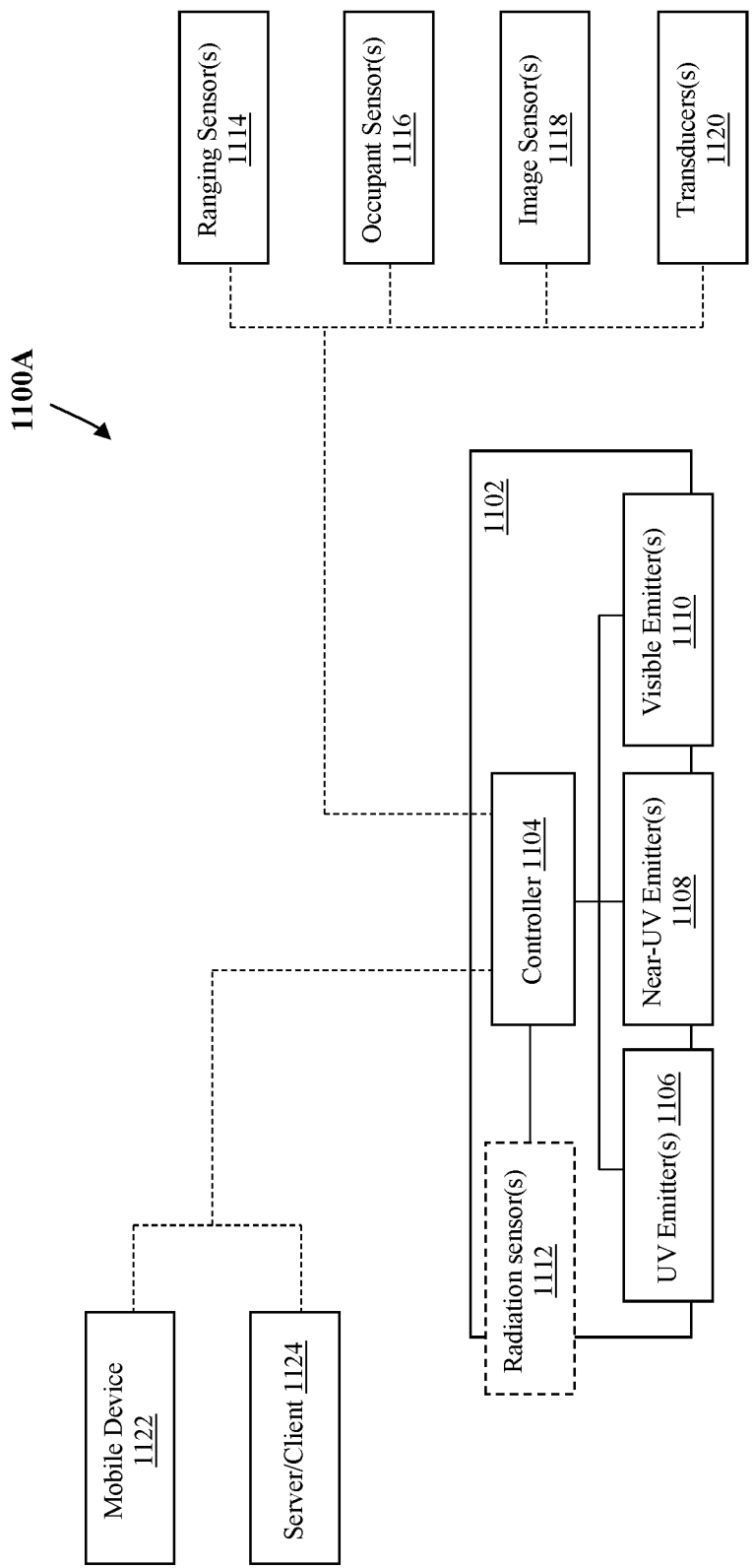
FIG. 11A is a functional block diagram of an apparatus and system for germicidal disinfection, in accordance with an embodiment.

Referring now to FIG. 11A, a functional block diagram of a germicidal disinfection apparatus and system 1100A is shown. In accordance with an embodiment, a germicidal disinfection apparatus and system 1100A may comprise a housing 1102, a controller 1104, at least one UV emitter 1106, at least one near-UV emitter 1108, and at least one visible emitter 1110. Housing 1102 may be configured to be retrofit into a ceiling grid or coupled to a ceiling junction box in an interior room of a building. UV emitter 1106, near-UV emitter 1108, and visible emitter 1110 may each comprise one or more types of light emitting devices, such as LEDs, electronic gas-discharge lamps, CFL lamps, and halogen lamps and the like. UV emitters 1106 may comprise a plurality of LEDs configured as an array. The plurality of LEDs may comprise one or more LEDs configured to produce a spectral output within a UV-A region (315-400 nanometers (nm)), a UV-B region (280-315 nm), and/or a UV-C region (100-280 nm). In certain embodiments, UV emitters 1106 comprises one or more LEDs configured to produce a spectral output within a UV-C region, and more particularly in a range of 250-270 nm. Near-UV emitters 1108 may comprise a plurality of LEDs configured as an array. Near-UV emitters 1108 may be configured to produce a visible light output within a near-UV region (e.g. 400-410 nm). In certain embodiments, near-UV emitters 1108 may be configured to produce a visible light output having a spectral wavelength of 405 nm. Visible emitter 1110 may comprise one or more lighting device configured to produce a visible light output having a spectral range between 400-700 nm. Visible emitter 1110 may comprise a plurality of LEDs configured as an array.

Figure 12A:
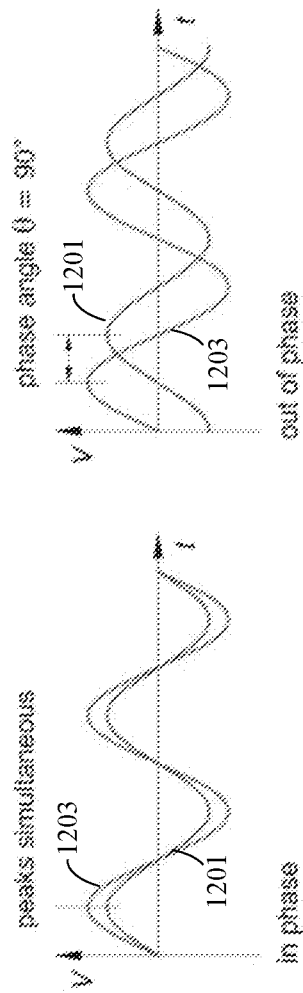
FIG. 12A is a sine wave plot of a UV emission and a near-UV emission being pulsed in-phase and out of phase.

In accordance with certain embodiments, controller 1104 may be operably engaged with UV emitters 1106, near-UV emitters 1108 and visible emitters 1110 via an electrical relay. Controller 1104 may comprise a processor and a memory device having instructions stored thereon to cause the processor to execute one or more control functions of controller 1104 to modulate a duty cycle of UV emitters 1106, near-UV emitters 1108 and/or visible emitters 1110; modulate a pulse width of UV emitters 1106, near-UV emitters 1108 and/or visible emitters 1110; and control/vary the phase of emission for UV emitters 1106 and near-UV-emitters 1108. For example, FIG. 12A shows a pulse wave 1201 of UV emitters 1106 and a pulse wave 1203 of near-UV emitters 1108 being modulated by controller 1104 to pulse a dual-band emission of UV radiation and near-UV radiation in-phase, in a first control setting, and out of phase, in a second control setting.

In accordance with certain embodiments, controller 1104 is operable to control emission of UV emitters 1106, near-UV emitters 1108 and visible emitters 1110 according to a first mode of operation and a second mode of operation. In a first mode of operation, controller 1104 is configured to modulate an emission of UV radiation and/or near-UV radiation from UV emitters 1106 and near-UV emitters 1108. In certain embodiments, the first mode of operation may be configured to pulse an emission from UV emitters 1106 and near-UV emitters 1108 and disengage emission from visible emitters 1110. In other embodiments, the first mode of operation may be configured to pulse an emission from each of UV emitters 1106, near-UV emitters 1108 and visible emitters 1110. In certain embodiments, controller 1104 is configured in the first mode of operation to modulate an emission of UV radiation and near-UV radiation from UV emitters 1106 and near-UV emitters 1108 to produce a dual band emission of radiation, either in-phase or out of phase. In certain embodiments, the first mode of operation may include pulsing the emission of UV radiation and near-UV radiation from UV emitters 1106 and near-UV emitters 1108 simultaneously (i.e. in phase) or in rapid or close succession (i.e. out of phase). In further configurations, the first mode of operation may include pulsing an emission from UV emitters 1106 and disengaging an emission from near-UV emitters 1108 in accordance with a first control setting; and pulsing an emission from near-UV emitters 1108 and disengaging an emission from UV emitters 1106 during a second control setting. In the second mode of operation, controller 1104 is configured to control and engage an emission of near-UV radiation from near-UV emitters 1108 and visible light from visible emitters 1110 and disengage a UV emission from UV emitters 1106.

In accordance with certain embodiments, controller 1104 may be communicably engaged with one or more radiation sensor 1112. Radiation sensor(s) 1112 may be coupled to, or otherwise contained within, housing 1102 and/or may be located independent from housing 1102 and communicably engaged with controller 1104 via a wireline or a wireless interface. Certain embodiments may comprise multiple radiation sensors 1112 being integral to housing 1102 and/or separate from housing 1102. Radiation sensors 1112 may comprise one or more closed-loop UV sensors, one or more closed-loop near-UV sensors, and/or one or more dual-band closed loop sensor being operable to measure both UV radiation and near-UV radiation. In an embodiment, radiation sensors 1112 may be configured and arranged such that radiation sensors 1112 are operable to measure an amount of UV radiation and near-UV radiation emitted from UV emitters 1106 and near-UV-emitters 1108 being reflected back to radiation sensors 1112 from a target surface of an interior room. Radiation sensors 1112 may provide a sensor input to controller 1104 in response to receiving the reflected radiation from the target surface of the interior room.

Controller 1104 may be configured to calculate an aggregate amount of radiation received by the target surface in response to the sensor input and determine whether a radiation threshold or target dose of radiation (i.e. a kill dose) has been delivered by UV emitters 1106 and/or near-UV emitters 1108 to the target surface. The radiation threshold or target dose of radiation may be calculated from a kinetic model or dose-response curve corresponding to a group of microorganisms (e.g., bacteria) or a specific microorganism (e.g., *Staphylococcus aureus*). Controller 1104 may have a plurality of target dose data stored in memory and may be configured to calculate a specific radiation threshold in response to a user configuration or other control input. Each kinetic model may include a dose-response curve for single band radiation (e.g. only UV radiation or only near-UV radiation) and dual band radiation (e.g. both UV radiation and near-UV radiation being emitted either in phase or out of phase, or otherwise in succession over a given time period).

Figure 12B:
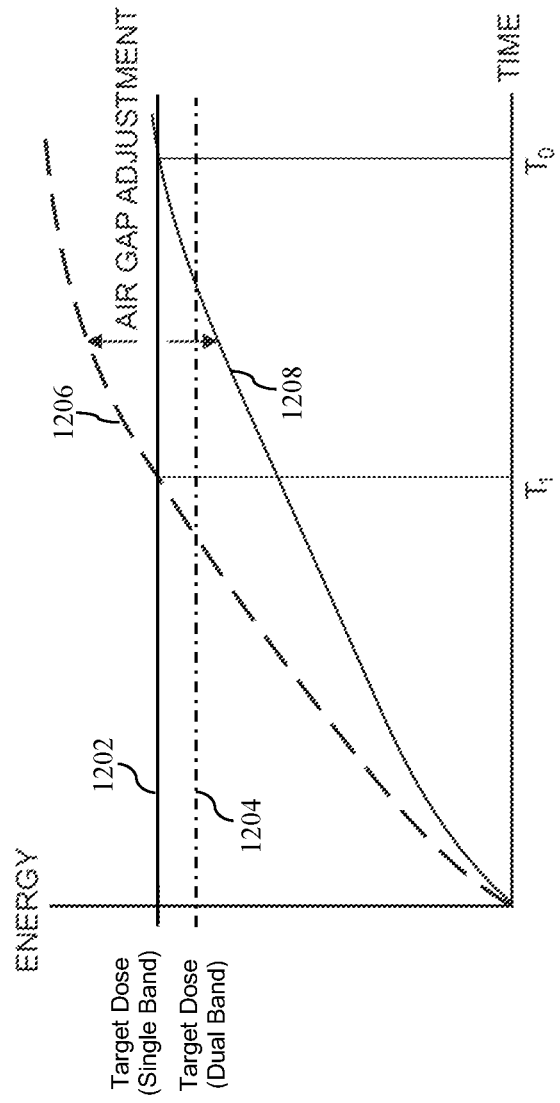
FIG. 12B is a plot of a target dose calculation for a single band emission and a dual band emission, as calculated with and without compensation for air gap.

In certain embodiments, controller 1104 may be communicably engaged with a ranging sensor 1114 being configured to measure a distance between the UV emitters 1106 and near-UV emitters 1108. Controller 1104 may be configured to process inputs from ranging sensor 1114 and calculate an amount of reflected energy lost as a function of distance to update the kinetic model and calculate the kill dose. For example, FIG. 12B shows an exemplary kinetic model comprising a dose-response curve 1206, a modified dose-response curve 1208 in response to a ranging sensor input, a single band target dose 1202, and a dual band target dose 1204.

In accordance with certain embodiments, controller 1104 may be communicably engaged with an occupant sensor 1116 configured to detect the presence of a person in an interior room in which system 1100A is installed and/or detect the proximity of a person to an emission zone of UV emitters 1106. Occupant sensor 1116 may include one or more sensor types, including but not limited to infrared sensors (IR), ultrasonic sensors, tomographic motion detection sensors, microwave sensors, camera-based sensors, environmental sensors (e.g. temperature, humidity and CO2 sensors), and the like. Controller 1104 may be configured to terminate an emission of UV emitters 1106 in response to an input from occupant sensor 1116 indicative of a person being in an interior room and/or in proximity to an emission zone of UV emitters 1106. In certain embodiments, controller 1104 may be communicably engaged with at least one image sensor 1118; for example, a digital camera. Image sensor 1118 may function as ranging sensor 1114 and/or occupant sensor 1116. Image sensor 1118 may provide image data to controller 1104 indicative of one or more situational or environmental conditions of an interior location. For example, controller 1104 may be configured to process image data to determine an occupant load of an interior space. Image sensor 1118 may be configured to capture body temperature data of occupants within an interior space. Controller 1104 may be configured to process body temperature data to determine a likelihood of one or more functional load for in the interior space (i.e. the likelihood and scope of microorganisms in the interior space) and estimate a target dose of UV radiation and/or near-UV radiation for the target space. In certain embodiments, controller 1104 is communicably engaged with at least one acoustic transducer 1120. Acoustic transducer 1120 may be configured to capture one or more sound inputs and communicate audio signal data to controller 1104. Controller 1104 may be configured to process the audio signal data to determine one or more situational or environmental conditions of the interior space.

In accordance with certain embodiments, controller 1104 may be communicably engaged with a mobile electronic device 1122 and/or a server/client device 1124 via a wireless or wireline communications interface. Mobile electronic device 1122 and/or server/client device 1124 may be configured to provide a user interface for configuring one or more control settings for controller 1104. Controller 1104 may be configured to communicate device data, sensor data, and usage data for mobile electronic device 1122 and/or server/client device 1124. Mobile electronic device 1122 and/or server/client device 1124 may be configured to communicate external data to controller 1104 to configure one or more control settings and/or update or provide one or more kinetic model.

Figure 11B:
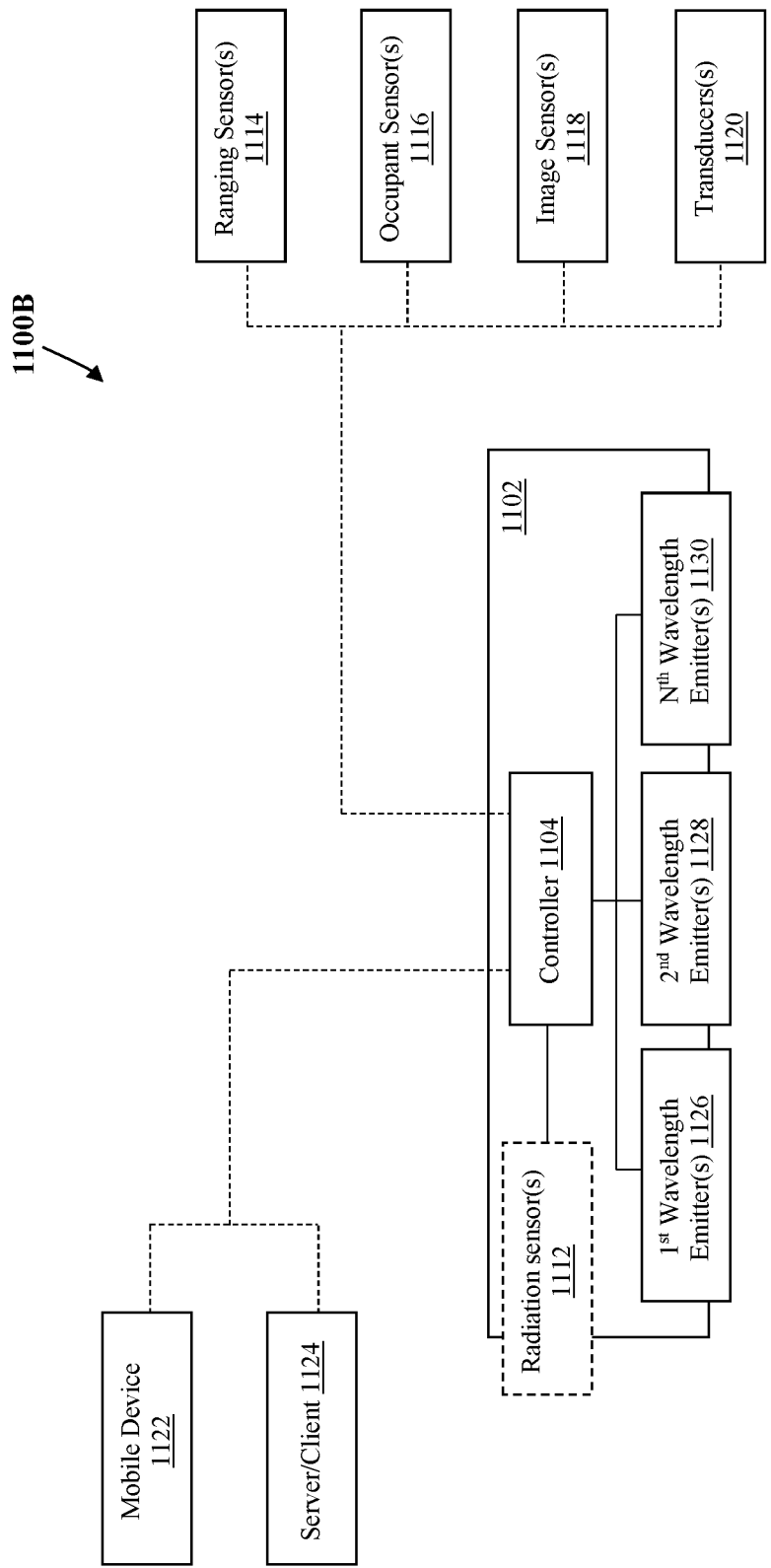
FIG. 11B is a functional block diagram of an apparatus and system for germicidal disinfection, in accordance with an embodiment.

Referring now to FIG. 11B with reference to FIG. 11A, a functional block diagram of a germicidal disinfection apparatus and system 1100B is shown. In accordance with various aspects of the present disclosure, apparatus and system 1100B may comprise the same elements as apparatus and system 1100A. According to certain aspects of the present disclosure, apparatus and system 1100B may comprise a plurality of emitters 1126 being configured to emit a first wavelength of light when operably engaged, a plurality of emitters 1128 being configured to emit a second wavelength of light when operably engaged, and one or more additional plurality of emitters 1130 being configured to emit an $N^{th}$ wavelength of light when operably engaged. In certain embodiments, emitters 1126 may be configured as UV emitters 1106 (FIG. 11A); emitters 1128 may be configured as Near-UV emitters 1108 (FIG. 11A); and emitters 1130 may be configured as visible light emitters 1110 (FIG. 11A). In accordance with certain aspects of the present disclosure, emitters 1126 may comprise one or more LED emitters configured to emit ultraviolet light at a wavelength in the range of 200 nm to 225 nm, i.e. Far-UV range. In certain embodiments, emitters 1126 may comprise one or more LED emitters configured to emit ultraviolet light at a wavelength in the range of 207 nm to 222 nm. In certain embodiments, emitters 1126 may comprise one or more LED emitters configured to emit ultraviolet light at a wavelength of 222 nm. In accordance with certain aspects of the present disclosure, emitters 1128 may comprise one or more LED emitters configured to emit ultraviolet light at a wavelength in the range of 200 nm to 280 nm, i.e. UV-C range. In certain embodiments, emitters 1126 may comprise one or more LED emitters configured to emit ultraviolet light at a wavelength in the range of 250 nm to 280 nm. In certain embodiments, emitters 1126 may comprise one or more LED emitters configured to emit ultraviolet light at a wavelength of 265 nm. In accordance with certain aspects of the present disclosure, emitters 1130 may comprise one or more LED emitters configured to emit light at a wavelength greater than or equal to 400 nm, i.e. visible light. In certain embodiments, emitters 1126 may comprise one or more LED emitters configured to emit ultraviolet light at a wavelength in the range of 400 nm to 405 nm. i.e. near UV range. In certain embodiments, emitters 1126 may comprise one or more LED emitters configured to emit ultraviolet light at a wavelength of 405 nm.

In accordance with certain aspects of the present disclosure, and still in reference to FIG. 11B, controller 1104 may be operably engaged with emitters 1126 to pulse an emission of Far-UV light according to one or more control settings. Controller 1104 may be further operably engaged with emitters 1128 to pulse an emission of UV-C light according to one or more control settings. Controller 1104 may be further operably engaged with emitters 1130 to pulse an emission of visible light according to one or more control settings. In accordance with various embodiments, controller 1104 may be configured to independently control the operation of each of emitters 1126, 1128 and 1130 according to one or more modes of operation. In certain modes of operation, controller 1104 may be configured to pulse an emission from emitters 1126, 1128 and 1130 substantially simultaneously. In other modes of operation, controller 1104 may be configured to pulse an emission from emitters 1126, 1128 and 1130 at separate/independent intervals. In accordance with certain embodiments, controller 1104 may be configured to modulate the duty cycle and phase (i.e. pulse width) of each of emitters 1126, 1128 and 1130 according to the one or more modes of operation. In certain embodiments, controller 1104 may be configured to select, configure and/or modify one or more modes of operations for emitters 1126, 1128 and 1130 according to one or more control settings and/or parameters being stored in memory. Controller 1104 may be further configured to select, configure and/or modify one or more modes of operations for emitters 1126, 1128 and 1130 according to one or more sensor inputs, user-generated inputs and/or external data inputs.

Figure 13:
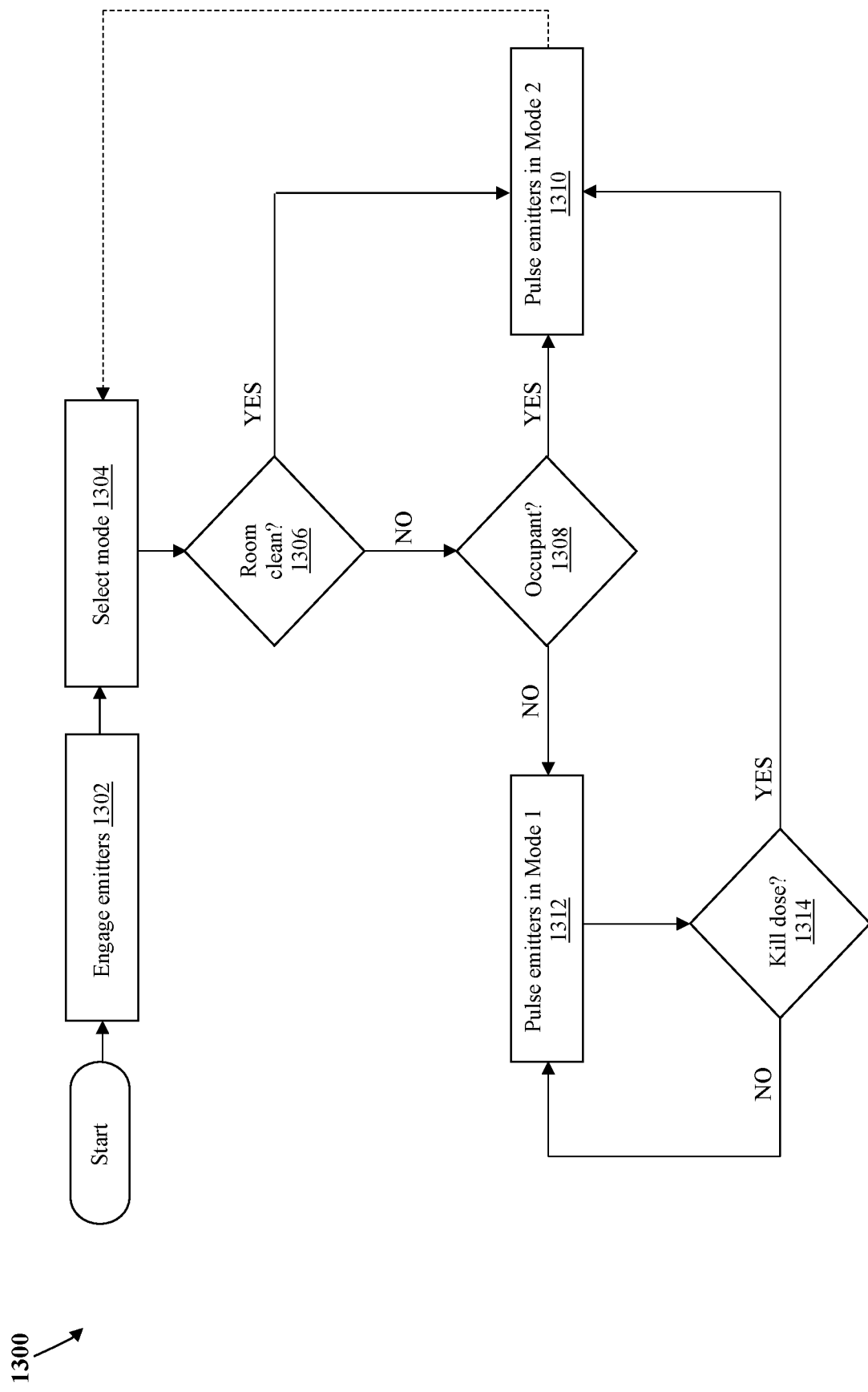
FIG. 13 is a functional block diagram of a routine for selecting between a first mode of operation and a second mode of operation of at least one light emitting device, in accordance with an embodiment.

Referring now to FIG. 13 (with reference to FIGS. 11A and 11B), a functional block diagram of a routine 1300 for selecting between a first mode of operation and a second mode of operation of controller 1104 is shown. In accordance with an embodiment, routine 1300 is initiated by engaging one or more UV emitters, near-UV emitters and visible light emitters 1302 (e.g., UV emitters 1106, near-UV emitters 1108 and visible emitters 1110). Step 1302 may include, for example, turning on a power switch for the emitters, engaging a control, or selecting a function setting from a user interface. Routine 1300 may continue by selecting a mode of operation 1304 for the controller. Certain embodiments may comprise a first mode of operation (Mode 1) and a second mode of operation (Mode 2), as described in the detailed description of FIGS. 11A and 11B, above. In accordance with certain embodiments, the first mode of operation is the default mode of operation. Routine 1300 may comprise a decision step 1306 to determine the disinfection status of a room (i.e. CLEAN or NOT CLEAN). The disinfection status of the room may be determined by evaluating one or more variables; for example, time elapsed since last disinfection cycle and changes in occupancy of the room since last disinfection cycle. If YES (i.e., the room is clean), then the controller selects the second mode of operation and engages the emitters in accordance with one or more control settings for Mode 2. If NO (i.e., the room is not clean), routine 1300 continues by executing a next decision step to determine if an occupant is present in a room and/or is within a zone of emission of UV emitters. If YES, the controller selects the second mode of operation and engages the emitters in accordance with one or more control settings for Mode 2. If NO, the controller selects the first mode of operation and engages the emitters in accordance with one or more control settings for Mode 1. Routine 1300 continues by executing a next decision step to determine if a kill dose of radiation has been received by the target surfaces. If NO, the controller continues to engage the emitters in accordance with one or more control settings for Mode 1. If YES, the controller executes the second mode of operation and engages the emitters in accordance with one or more control settings for Mode 2. Optionally, routine 1300 may continue by periodically repeating the decision logic to determine a mode of operation between Mode 1 and Mode 2. Routine 1300 may repeat itself at varying time intervals; for example, at a first time interval in response to a YES decision in step 1306 and at a second time interval in response to a YES decision in step 1308. Routine 1300 may also be continuously executed in response to the occurrence of one or more conditions; for example, a change in the occupancy status of a room from "occupied" to "unoccupied."

Figure 14:
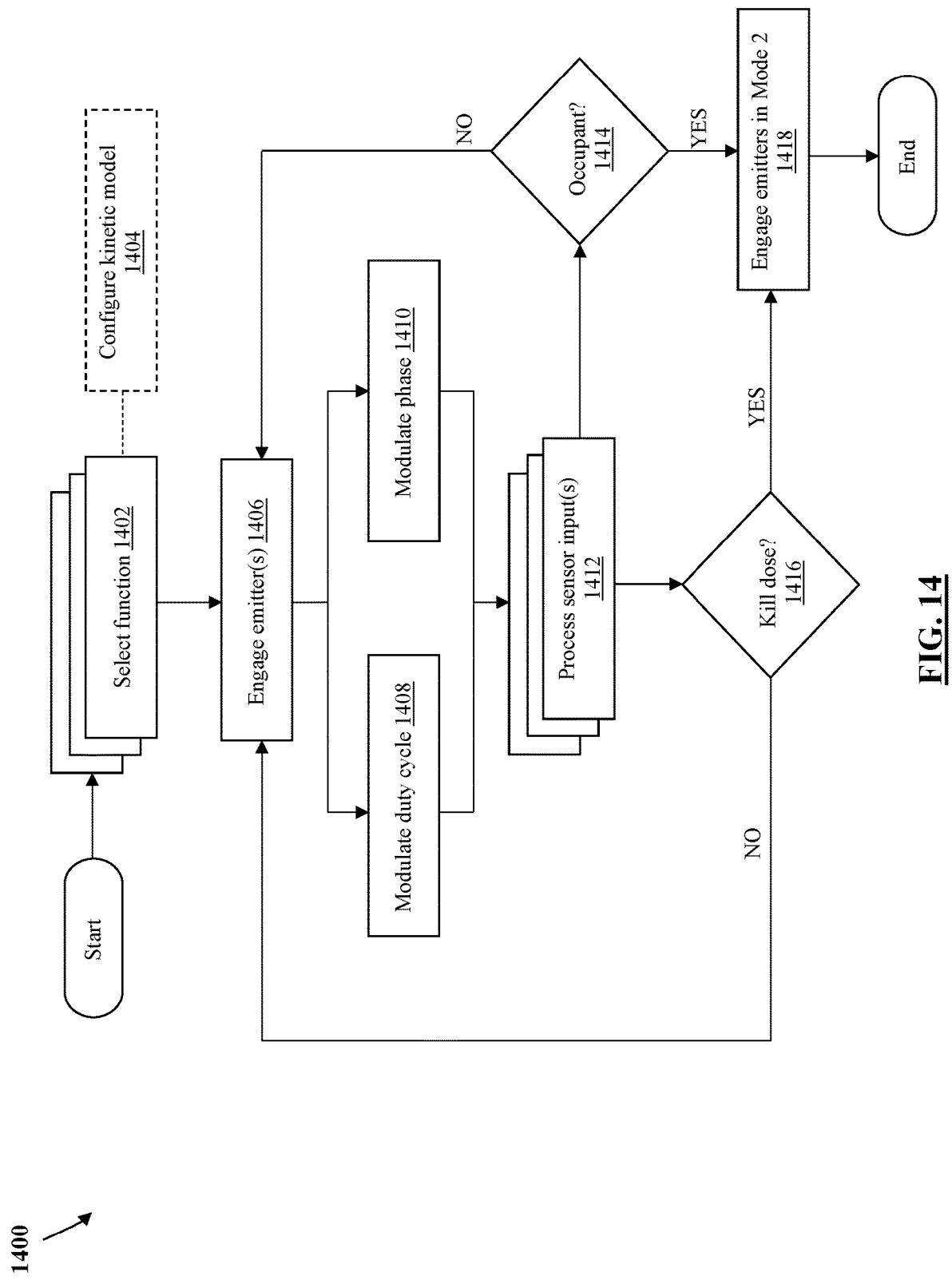
FIG. 14 is a functional block diagram of a routine for modulating a phase and duty cycle of at least one light emitting device, in accordance with an embodiment.

Referring now to FIG. 14 (with reference to FIGS. 11A and 11B), a functional block diagram of a routine 1400 for modulating a phase and duty cycle of at least one emitter within systems 1100A-B is shown. In accordance with an embodiment, routine 1400 commences by selecting a function 1402 of systems 1100A-B; for example, selecting an operational mode or configuring a target dosing variable corresponding to a specific group or type of microorganism. Optionally, step 1402 may concurrently comprise configuring a kinetic model in response to, or in conjunction with, selecting the function of systems 1100A-B. Routine 1400 may continue by engaging emitters in a first mode of operation or a second mode of operation 1406; for example, as described in routine 1300 of FIG. 13. Routine 1400 may continue in step 1408 by modulating the duty cycle of UV emitters 1106, near-UV emitters 1108 and visible emitters 1110; and may continue with step 1410 by modulating a phase of UV emitters 1106 and/or near-UV emitters 1108, such that UV emitters 1106 and near-UV emitters 1108 pulse emission in-phase according to a first modulation control and out of phase according to a second modulation control. Routine 1400 continues by processing one or more sensor inputs 1412 (e.g., a closed loop UV sensor input and an occupancy sensor input). Routine 1400 continues by executing decision steps 1414 and 1416. In decision step 1414, the controller processes the sensor input(s) to determine if an occupant is present in the room and/or in proximity to an emission area of UV emitters 1106. If NO, routine 1400 continues by engaging emitters in accordance with step 1406. If YES, the controller continues by engaging the emitters in accordance with one or more control settings for Mode 2 1418. In decision step 1416, the controller processes the sensor input(s) to determine if a kill dose has been delivered to the target surface(s) in the interior room. If NO, routine 1400 continues to engage emitters in accordance with step 1406. If YES, the controller engages the emitters in accordance with one or more control settings for Mode 2 1418.

Figure 15:
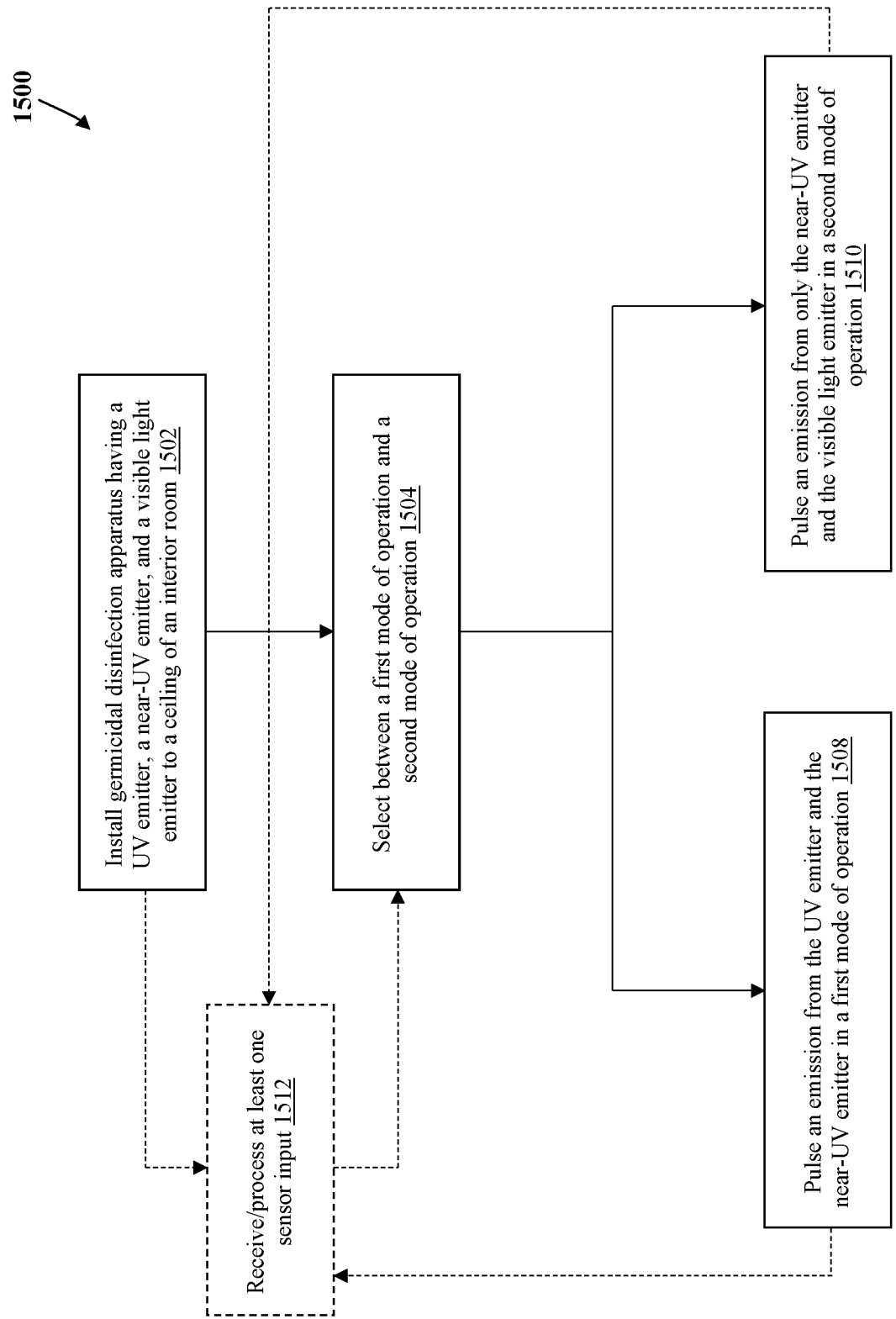
FIG. 15 is a process flow diagram of a method for controlling microorganisms in an interior environment, in accordance with an embodiment.

Referring now to FIG. 15 (with reference to FIGS. 11A and 11B), a process flow diagram of a method 1500 for controlling microorganisms in an interior environment is shown. In accordance with an embodiment, method 1500 comprises installing a germicidal disinfection apparatus having a UV emitter, a near-UV emitter, and a visible light emitter to a ceiling of an interior room 1502. In accordance with an embodiment, a germicidal disinfection apparatus may comprise germicidal disinfection apparatus 1100A. The UV emitter, near-UV emitter, and visible light emitter may comprise UV emitters 1106, near-UV emitters 1108 and visible emitters 1110. Method 1500 may continue by selecting between a first mode of operation and a second mode of operation 1504. In accordance with certain embodiments, step 1504 may comprise one or more steps of routine 1300 (as shown in FIG. 13). Depending on the outcome of step 1504, method 1500 may continue by pulsing an emission from the UV emitter, the near-UV emitter and, optionally, the visible light emitter in a first mode of operation 1508; or alternatively, method 1500 may continue by pulsing an emission from only the near-UV emitter and the visible light emitter in a second mode of operation 1510. Method 1500 may continue by receiving and processing at least one sensor input 1512. In response to receiving and processing at least one sensor input 1512, method 1500 may proceed to step 1504.

Figure 16:
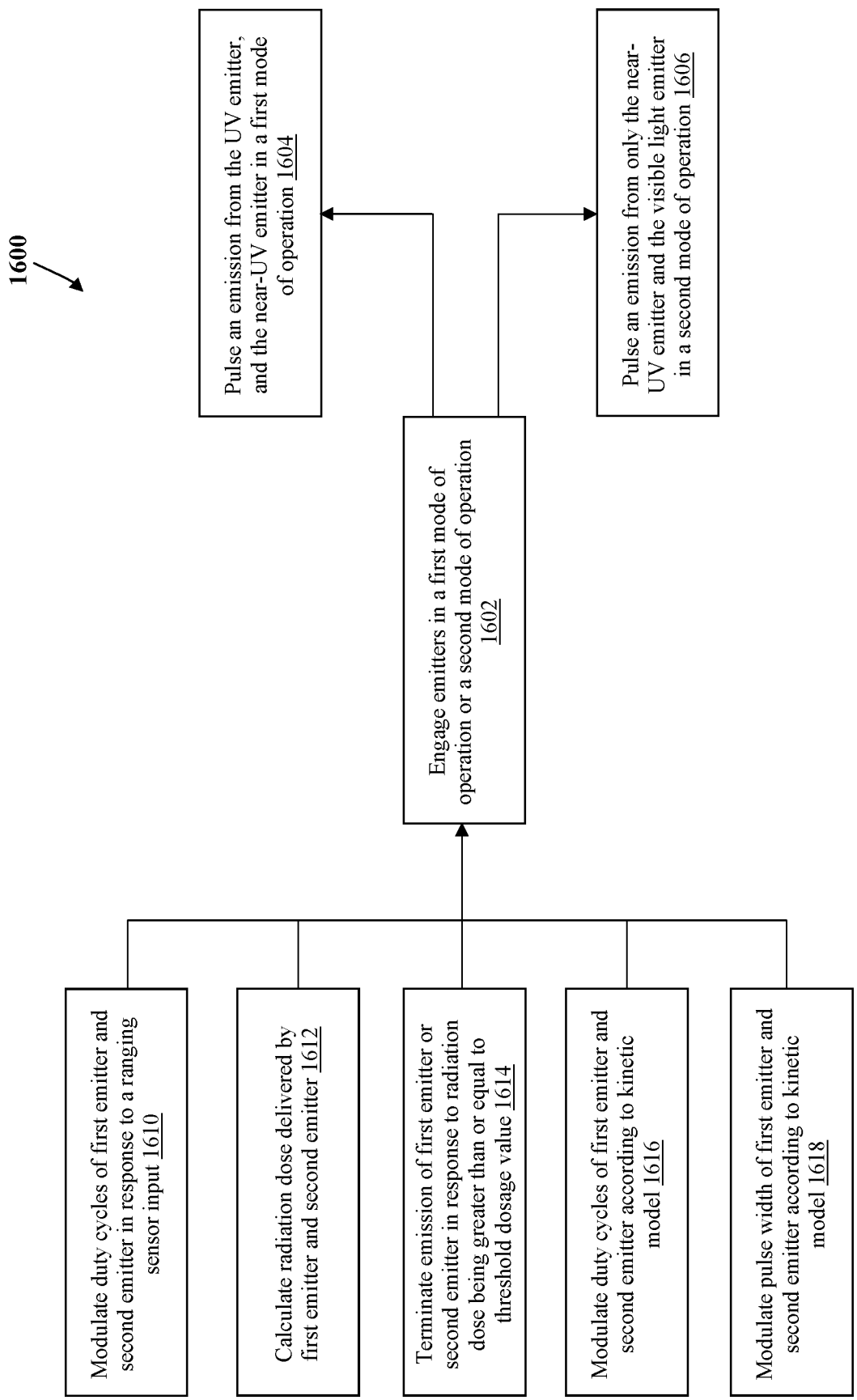
FIG. 16 is a process flow diagram of a method for controlling microorganisms in an interior environment, in accordance with an embodiment.

Referring now to FIG. 16, a process flow diagram of a method 1600 for controlling microorganisms in an interior environment is shown. In accordance with an embodiment, method 1600 may be a continuation from any one or more of the steps of method 1500. Method 1600 may commence with any combination of one or more of steps 1610-1618, which may be executed in a sequential order or non-sequential order and/or may be executed successively or concurrently. In accordance with an embodiment, method 1600 may execute step 1610 to modulate the duty cycles of the UV emitter(s) and the near-UV emitter(s) in response to a ranging sensor input. Method 1600 may execute step 1612 to calculate a radiation dose delivered by the UV emitter(s) and the near-UV emitter(s). Method 1600 may execute step 1614 to terminate emission of the UV emitter(s) and/or the near-UV emitter(s) in response to radiation dose being greater than or equal to threshold dosage value. Method 1600 may execute step 1616 to modulate the duty cycles of the UV emitter(s) and/or the near-UV emitter(s) according to a kinetic model. Method 1600 may execute step 1618 to modulate a pulse width of the UV emitter(s) and the near-UV emitter(s) according to a kinetic model. In response to executing one or more of steps 1610-1618, method 1600 may continue by engaging and/or disengaging the UV emitter(s), the near-UV emitter(s) and the visible light emitters in a first mode of operation or a second mode of operation 1602. In a first mode of operation, method 1600 may continue by pulsing an emission from the UV emitter(s), the near-UV emitter(s) and, optionally, the visible light emitter(s) 1604. In a second mode of operation, method 1600 may continue by pulsing an emission from only the near-UV emitter and the visible light emitter in a second mode of operation 1606 and disengaging an emission from the UV emitter(s).

Figure 17:
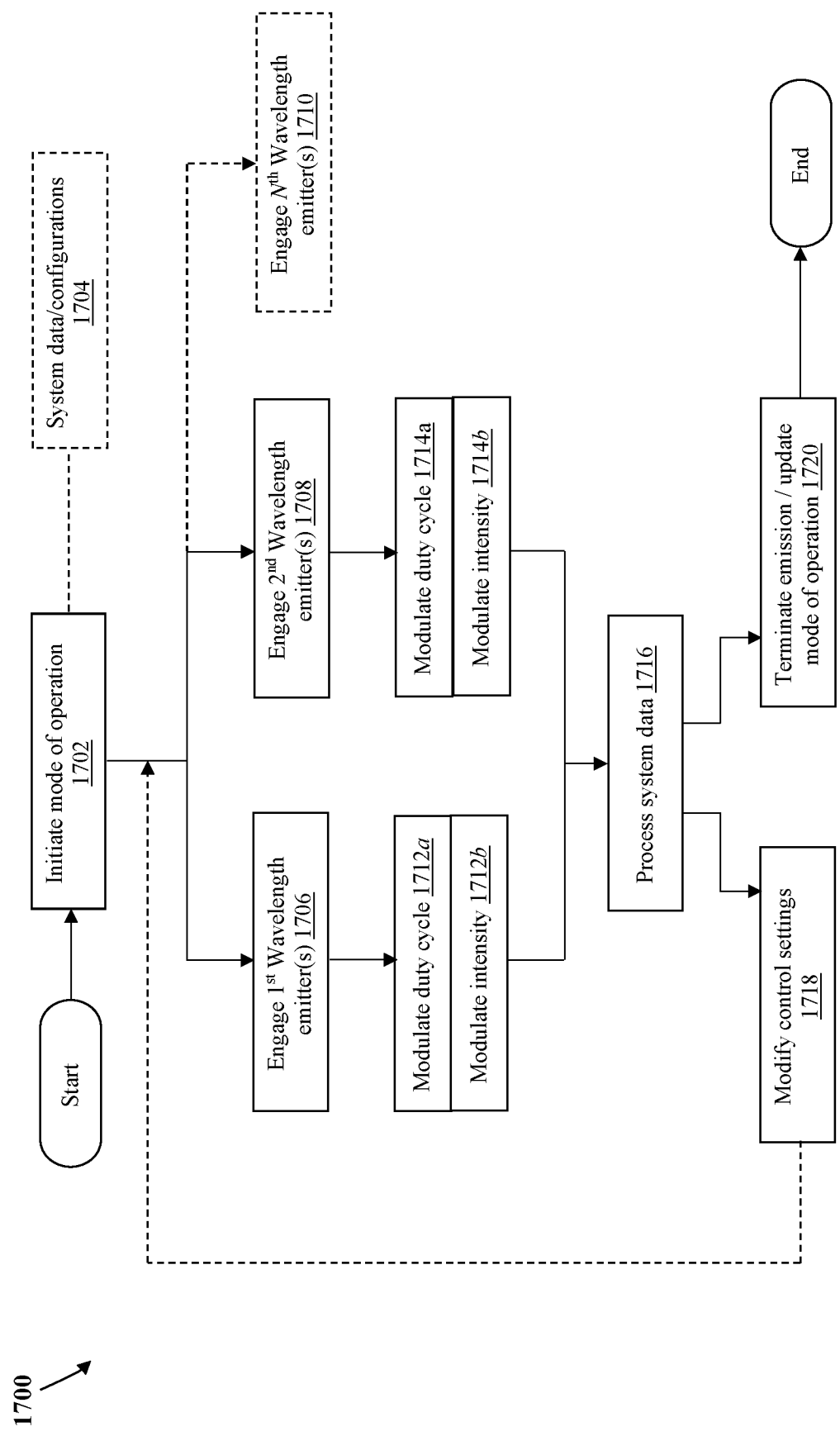
FIG. 17 is a process flow diagram of a routine for a mode of operation for at least one light emitting device, in accordance with an embodiment.

Referring now to FIG. 17, with reference to FIGS. 11A and 11B, a process flow diagram of a routine 1700 for a mode of operation for a germicidal disinfection device and system is shown. In accordance with certain aspects of the present disclosure, routine 1700 may be embodied within a set of instructions stored on a non-transitory computer-readable medium of controller 1104 (FIGS. 11A and 11B) that, when executed, cause at least one processor of controller 1104 to perform one or more actions associated with a mode of operation for controlling an emission from emitters 1126, 1128 and 1130 (FIGS. 11A and 11B) according to one or more control settings. In accordance with certain embodiments, routine 1700 is initiated upon executing one or more steps to initiate an operational mode 1702 of the controller. In accordance with certain embodiments, Step 1702 may comprise one or more steps for processing one or more of system data and/or system configurations 1704 being stored in a memory device of the controller. Upon initiating a mode of operation 1702, routine 1700 may proceed by executing one or more operations to operably engage at least one first emitter to pulse radiation comprising a first wavelength (Step 1706) and operably engage at least one second emitter to pulse radiation comprising a second wavelength (Step 1708). In accordance with certain aspects of the present disclosure, the first wavelength may be in the range of about 200 nm-225 nm (i.e. Far-UV range) and the second wavelength may be in the range of about 200 nm-280 nm (i.e. UV-C range). In an exemplary embodiment, the first wavelength is at or about 222 nm and the second wavelength is at or about 265 nm. In accordance with certain aspects of the present disclosure, routine 1700 may further comprise one or more operations to operably engage one or more subsequent emitter configured to pulse radiation at one or more distinct wavelength (i.e. $N^{th}$ wavelengths) from that of the first wavelength and the second wavelength (Step 1710). In certain embodiments, an $N^{th}$ wavelength from one or more subsequent emitter may be greater than or equal to 400 nm.

Still referring to FIG. 17, routine 1700 may comprise one or more steps for controlling one or more operations of the at least one first emitter and the at least one second emitter. In accordance with certain aspects of the present disclosure, routine 1700 may comprise one or more operations for modulating a duty cycle of the at least one first emitter (Step 1712a) and one or more operations for modulating an output intensity of the at least one first emitter (Step 1712b). Routine 1700 may further comprise one or more operations for modulating a duty cycle of the at least one second emitter (Step 1714a) and one or more operations for modulating an output intensity of the at least one second emitter (Step 1714b). Routine 1700 may comprise one or more operations for modulating the duty cycles of the at least one first emitter and the at least one second emitter to selectively pulse an emission of radiation from the at least one first emitter and the at least one second emitter in phase and out of phase depending on the control settings for the mode of operation. Modulating the duty cycles of the at least one first emitter and the at least one second emitter may further comprise disengaging the emission from the at least one first emitter and/or the at least one second emitter at designated intervals such that only one wavelength of radiation is being emitted at any given point in time during the mode of operation. In accordance with certain aspects of the present disclosure, routine 1700 may further comprise one or more operations for processing one or more sets of system data (Step 1716) to further configure one or more control settings for the mode of operation. In certain embodiments, the one or more sets of system data may comprise one or more of sensor data, user-generated data, device usage/operational data and/or one or more external data sets. In certain embodiments, an output of Step 1716 may comprise one or more operations for modifying or configuring one or more control settings for the at least one first emitter and the at least one second emitter (Step 1718). Another output of Step 1716 may comprise one or more operations for terminating the emission from the at least one first emitter and/or the at least one second emitter and/or updating or modifying the mode of operation for the controller (Step 1720).

Figure 18:
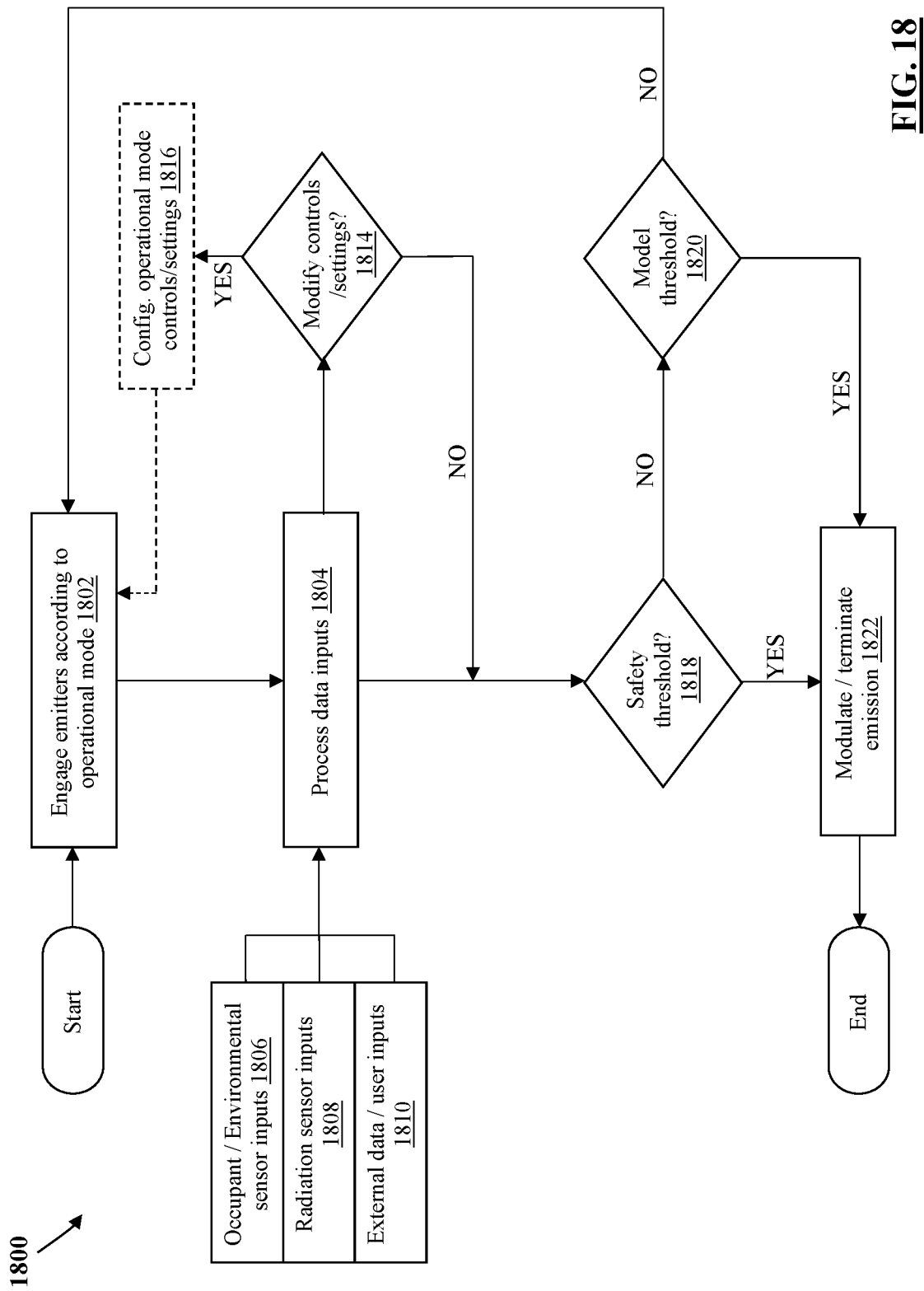
FIG. 18 is a process flow diagram of a routine for a mode of operation for least one light emitting device, in accordance with an embodiment.

Referring now to FIG. 18, with reference to FIGS. 11A and 11B, a process flow diagram of a routine 1800 for a mode of operation for a germicidal disinfection device and system is shown. In accordance with certain aspects of the present disclosure, routine 1800 may be sequential to routine 1700 and/or may comprise a sub-routine of routine 1700 (or vice versa). In accordance with certain embodiments, routine 1800 may be initiated upon executing one or more operations for engaging one or more emitters according to at least one operational mode. In an embodiment, the one or more emitters comprise one or more of emitters 1126, 1128 and 1130, as shown in FIG. 11B. Routine 1800 may continue by executing one or more operations for processing one or more data inputs from one or more data sources (Step 1804). In accordance with certain aspects of the present disclosure, the one or more data inputs may comprise one or more occupant and/or environmental sensor inputs 1806, one or more radiation sensor inputs 1808, and/or one or more external data sources or user-generated inputs 1810. In accordance with certain embodiments, Step 1804 may comprise one or more decision step(s) to determine whether to modify one or more operational controls or settings of the at least one operational mode based on the one or more data inputs (Step 1814). For example, a user of a germicidal disinfection device and system may configure one or more operational controls or settings via a user interface. If the outcome of Step 1814 is YES, then the routine 1800 may execute one or more operations to configure or modify one or more operational controls or settings for the at least one mode of operation (Step 1816). If the outcome of Step 1814 is NO, then routine 1800 may proceed to Step 1818. In accordance with certain embodiments, Step 1804 may comprise one or more decision step(s) to determine whether one or more safety threshold has been met/exceeded according to the operational mode (Step 1818). For example, an operational mode of the germicidal disinfection device and system may comprise one or more control settings for modulating a duty cycle and/or terminating an emission of one or more emitters according to a maximum dose threshold parameter (e.g. $\mu Ws/cm^2$) for the emission of one or more radiation wavelengths according to one or more conditions. For example, an operational mode of the germicidal disinfection device and system may be configured to engage a first group of emitters to pulse an emission of radiation at a wavelength of 222 nm and a second group of emitters to pulse an emission of radiation at a wavelength of 265 nm for a specified time period or dose. One or more safety control parameters may be configured to modify the duty cycle of one or more emitters and/or terminate an emission according to one or more safety conditions; for example, if an output from Step 1804 is indicative of one or more occupants being present within a zone of emission of the germicidal disinfection device and system. An exemplary safety control parameter may include, for example, a maximum allowable dose of radiation per wavelength, (e.g. $\mu Ws/cm^2$ threshold for 222 nm and $\mu Ws/cm^2$ threshold for 265 nm). In accordance with certain aspects of the present disclosure, if the output of Step 1818 is YES, routine 1800 may proceed by executing one or more operations to modulate or terminate an emission for one or more radiation wavelengths (Step 1822). For example, Step 1822 may comprise one or more operations for terminating an emission of radiation at the 265 nm wavelength and modulating a duty cycle of one or more emitters to reduce an intensity of emission at the 222 nm wavelength. If the output of Step 1818 is NO, routine 1800 may proceed by executing one or more data processing steps to determine whether an emission of radiation from the germicidal disinfection device and system meets or exceeds a threshold dose (e.g. $\mu Ws/cm^2$) associated with at least one kinetic model (Step 1820). In accordance with various aspects of the present disclosure, the at least one kinetic model comprise an effective germicidal dose of radiation for at least one microorganism. In certain embodiments, a threshold dose may comprise a threshold for a single band (i.e. single wavelength) emission of radiation (e.g. $\mu Ws/cm^2$ threshold for 222 nm) and/or a threshold for a dual/multi-band (i.e. more than one wavelength) emission of radiation (e.g. $\mu Ws/cm^2$ threshold for 222 nm and 265 nm, combined). In accordance with certain aspects of the present disclosure, if the outcome of Step 1820 is NO, then routine 1800 may execute one or more operations to continue to engage the one or more emitters according to the operational mode. If the outcome of Step 1820 is YES, then routine 1800 may execute one or more operations of Step 1822, as discussed above.

Referring now to FIG. 19, a process flow diagram of a method 1900 for controlling microorganisms in an interior environment is shown. In accordance with certain aspects of the present disclosure, method 1900 may comprise one or more steps of routine 1700 and/or routine 1800. Method 1900 may be initiated by engaging one or more emitters of a germicidal disinfection device and system according to at least one operational mode to pulse an emission of radiation comprising one or more wavelengths of ultraviolet light (Step 1902). In accordance with certain embodiments, a germicidal disinfection device and system may comprise germicidal disinfection apparatus and system 1100A or 1100B, as shown in FIGS. 11A and 11B. In an embodiment, the one or more emitters comprise one or more of emitters 1126, 1128 and 1130, as shown in FIG. 11B. According to certain aspects of the present disclosure, the one or more wavelengths of ultraviolet light may comprise a first wavelength within the Far-UV spectrum (i.e. 200 nm-225 nm) and a second wavelength within the UV-C spectrum (i.e. 200 nm-280 nm). In certain exemplary embodiments, the one or more wavelengths of ultraviolet light may comprise a first wavelength of 222 nm and a second wavelength of 265 nm. Method 1900 may proceed by executing one or more steps to modulate a phase or duty cycle of the one or more emitters (Step 1904). In accordance with certain aspects of the present disclosure, Step 1904 may comprise one or more steps for modulating the duty cycle of at least one first emitter and at least one second emitter to emit a single, dual and/or multi-band emission of radiation. Step 1904 may comprise one or more steps for modulating the duty cycle and phase of the at least one first emitter and the at least one second emitter such that the at least one first emitter and the at least one second emitter may pulse an emission of radiation either substantially simultaneously or substantially independently. Step 1904 may comprise one or more steps for modulating the phase of the at least one first emitter and the at least one second emitter such that the at least one first emitter and the at least one second emitter may pulse an emission of radiation in phase or out of phase. Method 1900 may continue by executing one or more steps for processing one or more sensor data inputs and/or other system data (Step 1906). In accordance with certain embodiments, the one or more sensor data inputs may comprise an input from at least one occupancy sensor and/or at least one radiation sensor. Method 1900 may continue by executing one or more steps to evaluate one or more emission threshold parameters (Step 1908) in response to processing the one or more sensor data inputs and/or other system data (Step 1906). In accordance with certain aspects of the present disclosure, the one or more emission threshold parameters may comprise one or more safety parameters and/or kinetic model parameters. Method 1900 may conclude by executing one or more steps to modify an operational mode of the controller and/or terminate an emission of radiation for the germicidal disinfection apparatus (Step 1910). In certain exemplary embodiments, Step 1910 may comprise one or more steps for pulsing an emission of 222 nm radiation from a first plurality of emitters and an emission of 265 nm radiation from a second plurality of emitters in response to an output from Step 1908 being indicative of the absence of occupants within an emission zone of the germicidal disinfection apparatus. Step 1910 may further comprise one or more steps for pulsing an emission of 222 nm radiation from the first plurality of emitters and terminating an emission of 265 nm radiation from the second plurality of emitters in response to an output from Step 1908 being indicative of the presence of occupants within an emission zone of the germicidal disinfection apparatus. Step 1910 may further comprise one or more steps for modulating a duty cycle of a first plurality of emitters and/or a second plurality of emitters to reduce an intensity of an emission of 222 nm radiation and/or 265 nm radiation in response to an output from Step 1908.

It will be evident to persons skilled in the art that the above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

Additionally, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

Although embodiments of the invention have been described with a certain degree of particularity, it is understood that the present disclosure is provided by way of example and that various changes to details of construction or arrangement of parts and even steps may be made without departing from the spirit or scope of the invention. The terms and expressions used herein have been employed as terms of description rather than terms of limitation, and their use is not intended as excluding equivalents of the features or steps described thereby.

The present disclosure includes that contained in the appended claims as well as that of the foregoing description. Although this invention has been described in its exemplary forms with a certain degree of particularity, it is understood that the present disclosure of has been made only by way of example and numerous changes in the details of construction and combination and arrangement of parts may be employed without departing from the spirit and scope of the invention.

What is claimed is:

1. A germicidal disinfection apparatus comprising:
a housing;
at least one first emitter coupled to the housing and configured to emit ultraviolet light at a first wavelength in the range of 207 to 225 nanometers;
at least one second emitter coupled to the housing and configured to emit ultraviolet light at a second wavelength between 200 and 280 nanometers; and
a controller operably engaged with the at least one first emitter to pulse a first emission of ultraviolet light comprising the first wavelength and operably engaged with the at least one second emitter to pulse a second emission of ultraviolet light comprising the second wavelength,
wherein the controller is configured to selectively modulate a duty cycle and phase of the at least one first emitter and the at least one second emitter,
wherein the controller is further configured to modulate the duty cycle and/or the phase of one or both of the at least one first emitter and the at least one second emitter according to a kinetic model associated with at least one microorganism.

2. The apparatus of claim 1 further comprising at least one third emitter coupled to the housing and configured to emit visible light at a third wavelength of greater than 400 nanometers.

3. The apparatus of claim 1 further comprising at least one sensor configured to detect the presence of an occupant within an emission zone of the at least one first emitter and the at least one second emitter, the at least one sensor being operably engaged with the controller to communicate a sensor input.

4. The apparatus of claim 1 wherein the controller is configured to selectively modulate the at least one first emitter and the at least one second emitter to pulse the first emission of ultraviolet light and the second emission of ultraviolet light in phase or out of phase.

5. The apparatus of claim 1 wherein the first wavelength is 222 nm and the second wavelength is 265 nm.

6. The apparatus of claim 3 wherein the controller is configured to modulate the duty cycle of the at least one first emitter according to at least one control setting in response to the sensor input from the at least one sensor.

7. The apparatus of claim 3 wherein the controller is configured to modulate the duty cycle of the at least one second emitter according to at least one control setting in response to the sensor input from the at least one sensor.

8. A method for controlling microorganisms in an interior environment comprising:
deploying the germicidal disinfection apparatus of claim 1 in the interior environment;
pulsing, in a first mode of operation, a first emission of ultraviolet light from the at least one first emitter and the at least one second emitter; and
pulsing, in a second mode of operation, a second emission of ultraviolet light from the at least one first emitter and the at least one second emitter;
wherein the first mode of operation comprises modulating the duty cycle and phase of the at least one first emitter and the at least one second emitter according to a first plurality of control settings, and
wherein the second mode of operation comprises modulating the duty cycle and phase of the at least one first emitter and the at least one second emitter according to a second plurality of control settings.

9. The method of claim 8 further comprising calculating a radiation dose delivered by the at least one first emitter and the at least one second emitter.

10. The method of claim 9 further comprising terminating an emission from the at least one first emitter or the at least one second emitter in response to the radiation dose being greater than or equal to at least one maximum radiation exposure limit for an occupant.

11. The method of claim 8 further comprising modulating the duty cycle and/or phase of one or both of the at least one first emitter and the at least one second emitter according to the kinetic model associated with the at least one microorganism.

12. The method of claim 11 further comprising modulating the pulse width of an emission from the at least one first emitter and/or an emission from the at least one second emitter according to the kinetic model associated with the at least one microorganism.

13. A germicidal disinfection system comprising:
a housing;
at least one first emitter coupled to the housing and configured to emit ultraviolet light at a first wavelength in the range of 207 to 225 nanometers;
at least one second emitter coupled to the housing and configured to emit ultraviolet light at a second wavelength between 200 and 280 nanometers;
a radiation sensor; and
a controller operably engaged with the at least one first emitter and the at least one second emitter, the controller comprising at least one microprocessor configured to perform one or more operations for controlling an emission of ultraviolet light from the at least one first emitter and the at least one second emitter,
wherein the one or more operations comprise operations for selectively modulating a duty cycle and phase of the at least one first emitter and the at least one second emitter,
wherein the one or more operations comprise operations for modulating the duty cycle of the at least one first emitter and the at least one second emitter in response to a sensor input from the radiation sensor.

14. The system of claim 13 wherein the one or more operations comprise operations for modulating the duty cycle of the at least one first emitter and the at least one second emitter in response to a sensor input from at least one occupant sensor communicably engaged with the controller.

15. The system of claim 13 wherein the one or more operations comprise operations for modulating the duty cycle and/or phase of one or both of the at least one first emitter and the at least one second emitter according to a kinetic model associated with at least one microorganism.

16. A germicidal disinfection system comprising:
at least one first emitter configured to emit ultraviolet light at a first wavelength in the range of 207 to 225 nanometers;
at least one second emitter configured to emit ultraviolet light at a second wavelength between 200 and 280 nanometers;
a controller operably engaged with the at least one first emitter and the at least one second emitter to pulse an emission of ultraviolet light comprising the first wavelength from the at least one first emitter and pulse an emission of ultraviolet light comprising the second wavelength from the at least one second emitter according to one or more control parameters,
wherein the one or more control parameters comprise parameters for modulating a duty cycle of the at least one first emitter and the at least one second emitter and parameters for modulating a phase of the at least one first emitter and the at least one second emitter; and
at least one radiation sensor communicably engaged with the controller,
wherein the one or more control parameters comprise parameters for modulating the duty cycle of the at least one first emitter and the at least one second emitter in response to a sensor input from the at least one radiation sensor.

17. The system of claim 16 further comprising at least one third emitter configured to emit visible light at a third wavelength of greater than 400 nanometers.

18. The system of claim 16 wherein the one or more control parameters comprise parameters for modulating the duty cycle and/or phase of one or both of the at least one first emitter and the at least one second emitter according to a kinetic model associated with at least one microorganism.

19. The apparatus of claim 1 further comprising at least one radiation sensor communicably engaged with the controller.

20. The apparatus of claim 19 wherein the controller is further configured to modulate the duty cycle of the at least one first emitter and the at least one second emitter in response to a sensor input from the at least one radiation sensor.

* * * * *